(12) United States Patent
De Leij et al.

(10) Patent No.: US 9,743,675 B2
(45) Date of Patent: Aug. 29, 2017

(54) ANTIMICROBIAL COMPOSITION

(75) Inventors: Franciscus Antonius Anna Maria De Leij, Guildford (GB); Mina Kalantarzadeh, Guildford (GB); Dulcie Mulholland, Guildford (GB); Tony Hutchings, Alton (GB)

(73) Assignee: UNIVERSITY OF SURREY, Surrey (GB)

( * ) Notice: Subject to any disclaimer, the term of this patent is extended or adjusted under 35 U.S.C. 154(b) by 0 days.

(21) Appl. No.: 13/395,415

(22) PCT Filed: Sep. 10, 2010

(86) PCT No.: PCT/GB2010/051517
§ 371 (c)(1),
(2), (4) Date: May 29, 2012

(87) PCT Pub. No.: WO2011/030158
PCT Pub. Date: Mar. 17, 2011

(65) Prior Publication Data
US 2013/0045954 A1    Feb. 21, 2013

(30) Foreign Application Priority Data
Sep. 10, 2009  (GB) .................................. 0915879.1

(51) Int. Cl.
*A01N 35/04*    (2006.01)
*A01N 65/00*    (2009.01)
*A01N 65/06*    (2009.01)
*A61K 45/06*    (2006.01)

(52) U.S. Cl.
CPC ............ *A01N 65/06* (2013.01); *A01N 35/04* (2013.01); *A01N 65/00* (2013.01)

(58) Field of Classification Search
USPC ............................. 514/171, 171 M, 557, 574
See application file for complete search history.

(56) References Cited

U.S. PATENT DOCUMENTS

| | | | |
|---|---|---|---|
| 3,980,050 A | 9/1976 | Neubauer | |
| 4,177,288 A * | 12/1979 | Gohlke | 514/500 |
| 4,560,527 A | 12/1985 | Harke et al. | |
| 4,883,663 A * | 11/1989 | Leon Leon | 424/757 |
| 5,227,163 A | 7/1993 | Eini et al. | |
| 8,901,245 B2 * | 12/2014 | Tang et al. | 525/54.42 |
| 8,993,618 B2 * | 3/2015 | Wu | A61K 31/353 514/449 |
| 2005/0100520 A1 | 5/2005 | Hagura et al. | |

FOREIGN PATENT DOCUMENTS

| | | |
|---|---|---|
| DE | 195 23 320 A1 | 1/1997 |
| DE | 19831288 A1 | 1/2000 |
| JP | 7 048530 A | 2/1995 |
| WO | WO 00/09172 A1 | 2/2000 |
| WO | 02/098439 A1 | 12/2002 |
| WO | 03/028451 A2 | 4/2003 |

OTHER PUBLICATIONS

Oh, Hyun Jeong et al. (HCAPLUS, abstract of Korean Society of Applied Biological Chemistry (2007),50(3), 164-169).*
Lee et al., abstract of Journal of Microbiology and Biotechnology (2008),18(3), 497-502).*
Rupasinghe et al. (Food Research International 39 (2006) 575-580).*
Soderberg et al. (Toxicology 107 (1996) 99-109).*
Sato et al. (Canadian Journal of Chemistry, vol. 42 (1964), pp. 635-640).*
International Search Report and Written Opinion issued on Dec. 23, 2011 for International Application No. PCT/GB2010/051517.
100 Mesh (on the internet at en.wikipedia.org/wiki/mesh_(scale) (downloaded on Oct. 3, 2013)).
Mimosa Tenuiflora Poir (on the internet at web.archive.org/web/20080329192757/en.wikipedia.org/wiki/Mimosa_tenuiflora (archived on Mar. 29, 2008)).
Stem (on the internet at en.wikipedia.org/wiki/bark (downloaded on Oct. 3, 2013)).

\* cited by examiner

*Primary Examiner* — Sabiha N Qazi
(74) *Attorney, Agent, or Firm* — Knobbe, Martens, Olson & Bear, LLP

(57) ABSTRACT

Antimicrobial compositions comprising a terpenoid in combination with an antimicrobial agent are provided. In addition, uses of such compositions in various applications involving preventing, combating or treating microbial infections, or preventing microbial growth or establishment are provided.

7 Claims, 4 Drawing Sheets

Figure: 1
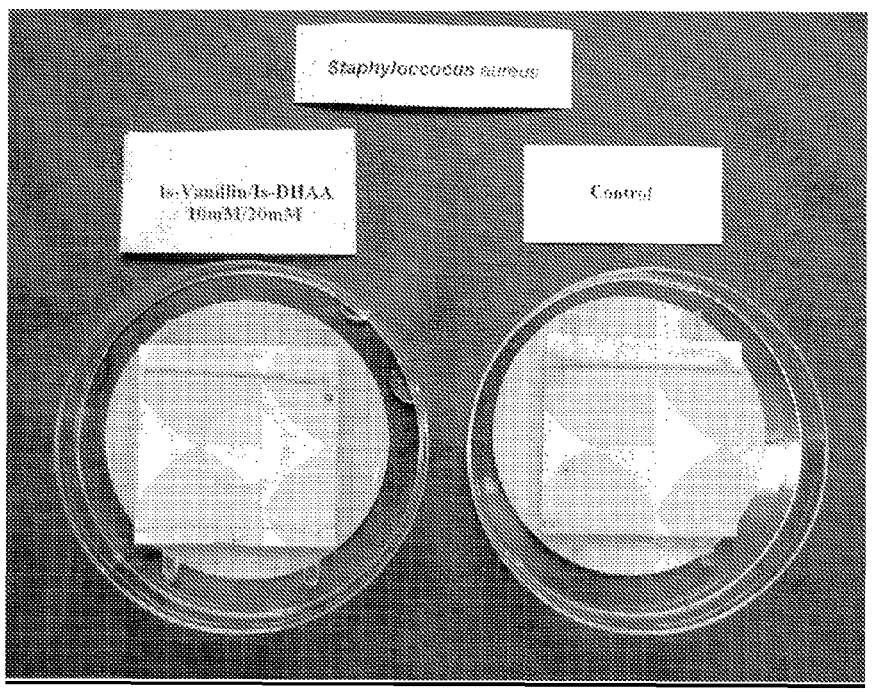
Figure: 2
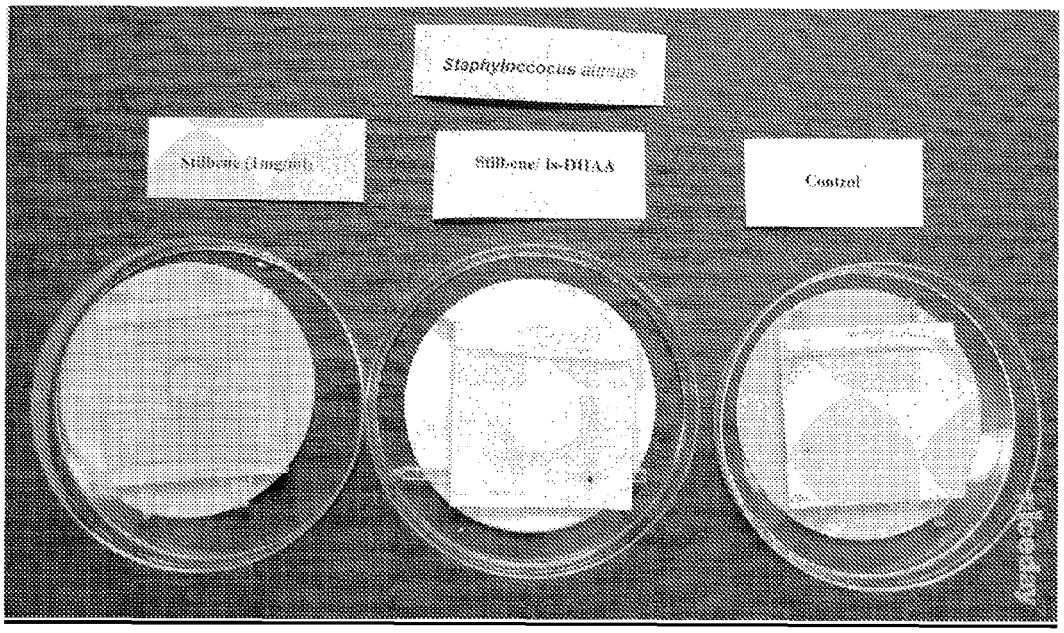

Figure: 3
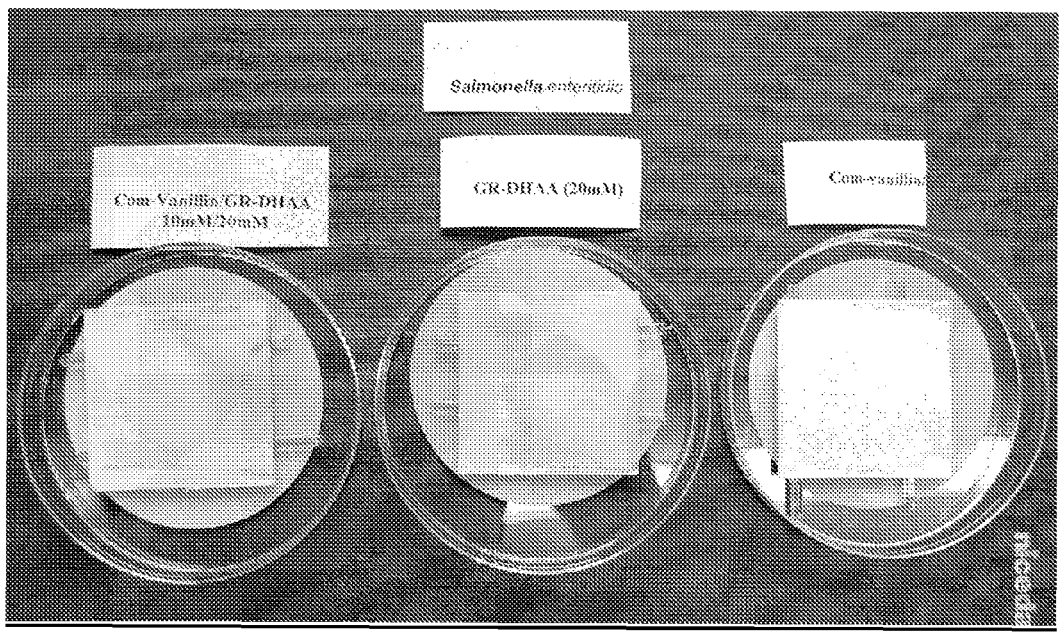
Figure: 4
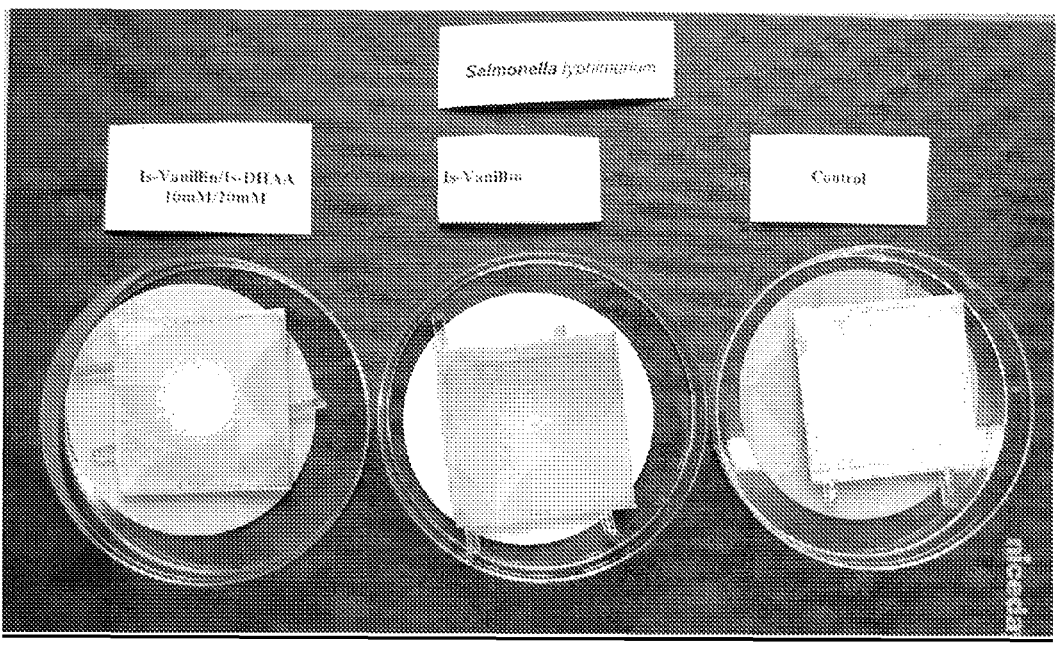

Figure: 5
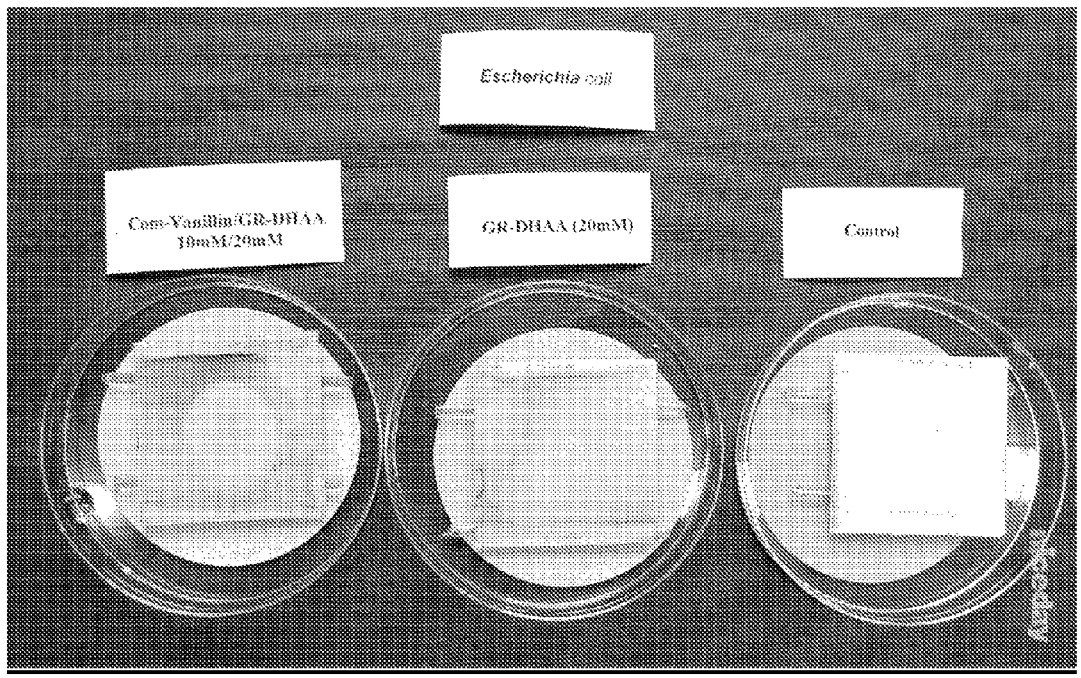
Figure: 6
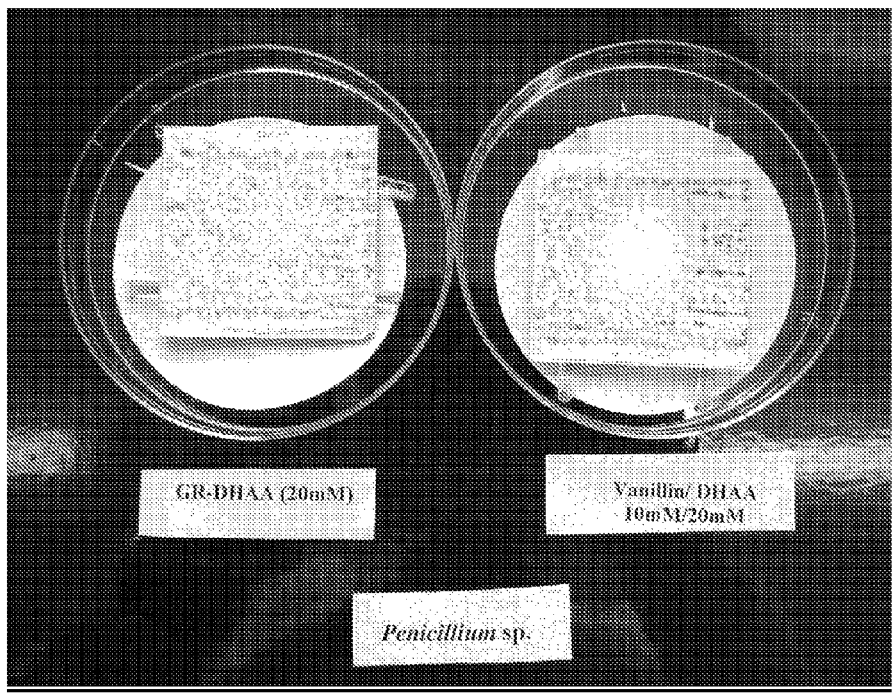

Figure: 7
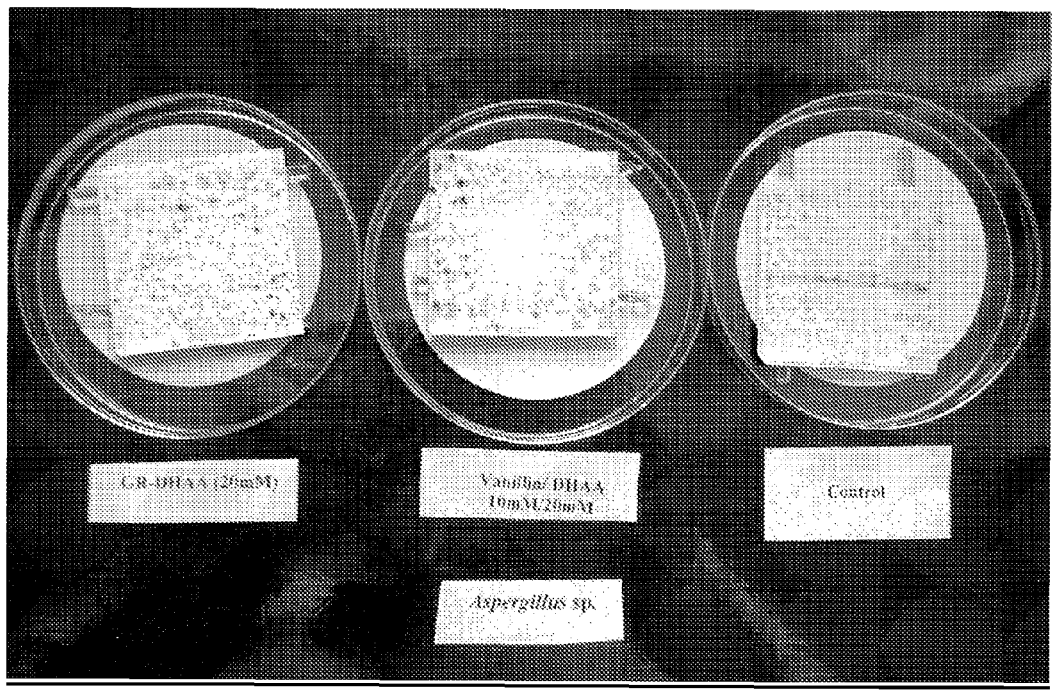
Figure: 8
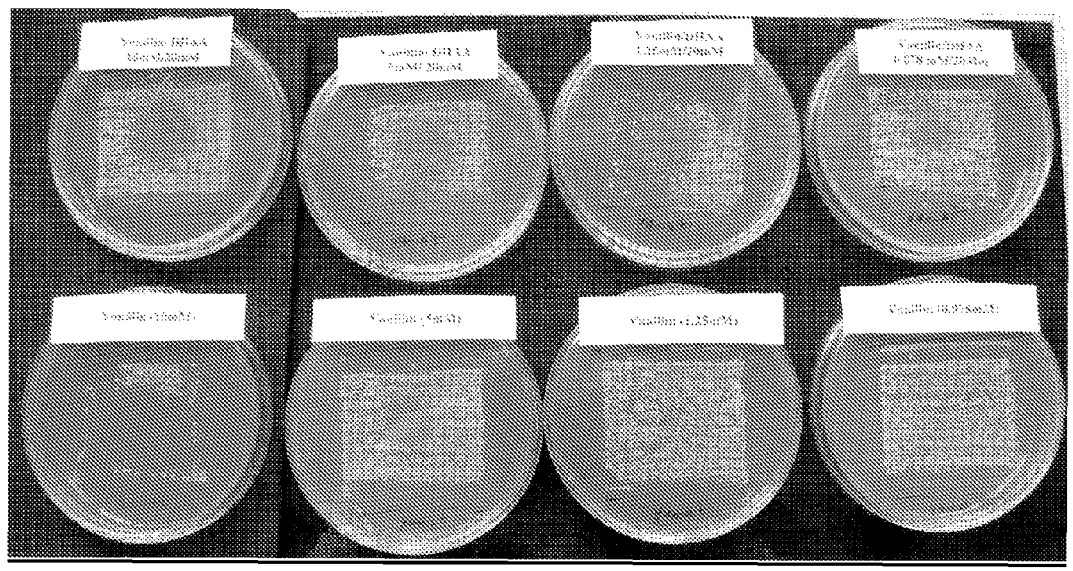

ANTIMICROBIAL COMPOSITION

RELATED APPLICATIONS

This application is a U.S. National Phase of International Application No. PCT/GB2010/051517, filed Sep. 10, 2010, designating the U.S., and published as WO 2011/030158 on Mar. 17, 2011 which claims the benefit of British Patent Application No. 0915879.1 filed Sep. 10, 2009.

The present invention relates to antimicrobial compositions. In particular, the invention relates to antimicrobial compositions comprising a terpenoid in combination with an antimicrobial agent, and to the uses of such compositions in various applications involving preventing, combating or treating microbial infections, or preventing microbial growth or establishment. Particular applications of the antimicrobial composition include uses in the animal bedding industry such as in poultry houses, in general antimicrobial products such as in antiseptics and disinfectants, in the food industry such as packaging materials and for the direct treatment of produce, for application to soil, mulches or plant material to prevent the spread of plant pathogens, and can be used for a wide variety of medical applications.

In poultry houses, microbial activity in the bedding material results in the conversion of uric acid in chicken faeces into ammonia. This is a particular problem in poultry houses with high stocking densities, where the high concentrations of ammonium in the litter result in it becoming alkaline. This results in the conversion of ammonium into ammonia gas, which, at elevated concentrations, is toxic to the birds and when released into the atmosphere is an important contributor to acid rain. Ammonia emissions from animal houses are therefore under scrutiny, and new laws are forcing farmers to comply with strict emission regulations (IPPC). In practical terms, implementation of IPPC means that farms that have more than 40,000 birds must: (i) minimise emissions of ammonia, (ii) reduce associated odour from poultry houses, and (iii) have a manure management plan in place.

Poultry reared on bedding that is rich in ammonium can suffer from 'caustic burns' to their feet and chest as well as foot pad dermatitis (FPD), which reduce the quality of the resultant food product. Prevention of 'caustic burns' caused by ammonium not only improves animal welfare, but will also reduce farmer's losses as a result of better animal growth and higher quality animal products. There is therefore a need to minimise microbial activity in poultry houses.

Reduction of microbial activity to prevent microbial conversion of uric acid into ammonia and ammonium in animal bedding is currently achieved by keeping the moisture content of the bedding as low as possible. Reports that claim to be effective in this respect use bedding materials that adsorb moisture. However, in practice, it is difficult to maintain low moisture levels in the bedding, as high bird stocking densities are often used, and because condensation and liquid spills occur which result in the bedding becoming increasingly wet. This moisture supports microbial activity, which results in the formation of ammonium from the uric acid that is present in the chicken faeces.

Ammonium is converted into ammonia when the pH rises above pH 7, with concentrations of ammonia becoming significant above pH 8. To prevent the bedding material becoming caustic once the uric acid is converted into ammonia, acidic salts, such as alum $(KAl(SO_4)_2.12H_2O)$ or sodium-bisulphate, may be added to maintain a low pH. However, these compounds do not last, and are costly to the farmer. Furthermore, large amounts of aluminium in the resulting litter, creates waste disposal problems due to elevated heavy metal concentrations. As a result, use of such 'acidifying substances' is not common, and ammonia formation in poultry houses is commonplace.

Another problem with animals, such as of chickens, that are reared for their meat or for eggs, is the risk of food-borne pathogens. It is estimated that 75-95% of frozen chickens that are sold in supermarkets are infected with *Campylobacter*, and that 10% are infected with *Salmonella*. For farmers producing breeding and laying flocks, detection of *Salmonella* in an animal house now means that the whole flock will need to be destroyed resulting in significant economic losses to the farmer. It is thought that these bacteria find their way from the animal house, and in particular the bedding, into the animal itself. It is believed that the cause of these problems is that animal bedding provides a suitable substrate for these bacteria, which includes high temperatures (25-35° C.), high moisture levels and high concentrations of nutrients found in the faeces, and pH values well within the growth range of these bacteria. Accordingly, there is a significant need to reduce the amount of microbial activity within animal bedding to prevent the growth of these pathogens.

*Fusobacterium necrophorum* and *Bacteroides melaninogenicus* are the causal agents of foot root (pododematitis), a condition where the area between the toes of sheep, goats and cattle becomes infected and causes the hoof to rot away. The condition is very painful and contagious. Animal beddings that would cause the bacteria to be killed upon contact would significantly reduce the harm these bacteria inflict upon animals with cloven hoofs.

There is a wide range of synthetic disinfectants and disinfectants on the market that can be characterised as being based on alcohols, aldehydes, oxidising agents, phenolics or quaternary ammonium compounds. Such substances are, in general, effective at killing micro-organisms, but suffer from the following problems: (i) bacteria develop resistance to aldehydes; (ii) oxidising agents and phenolics are extremely corrosive; (iii) aldehydes are inactivated by organic matter; (iv) alcohols are non-persistent; (v) most of them are toxic, or act as irritants, to humans; or (vi) they have a negative environmental impact.

Due to the above problems, a large demand has developed for 'natural' and more 'green' antimicrobial agents, such as essential oils and other natural products with anti-microbial properties, such as vanillin. Common examples of essential oils include thymol (a natural phenolic product derived from thyme), products with tea tree oil, and products that incorporate other essential oils derived from cloves (eugenol), eucalyptus, pine, etc. However, essential oils and other plant-derived anti-microbial products tend to be only weakly antimicrobial and so, in order to be effective, concentrations need to be high giving these products a strong smell, which is not only expensive but can be very off-putting to the user. There is therefore a need in the art to increase the activity of known antimicrobial agents.

The inventors have now determined that terpenoids and derivatives thereof significantly improve the antimicrobial properties of known antimicrobial agents.

Thus, according to a first aspect of the invention, there is provided an antimicrobial composition comprising a terpenoid or a derivative thereof, and an antimicrobial agent, which agent interferes with cell membrane integrity or with protein synthesis.

In a second aspect, there is provided use of a terpenoid or a derivative thereof for increasing the antimicrobial activity of an antimicrobial agent, which agent interferes with cell membrane integrity or with protein synthesis.

The inventors investigated the mechanisms by which mildly heated wood shavings become antimicrobial, and surprisingly observed that extracts from these shavings that contained both the terpenoid, dehydroabietic acid, and the antimicrobial agent, vanillin, were highly bacteriocidal. However, as described in Example 1, what was most surprising was that they found that the extract containing both substances exhibited antimicrobial activity which was more than 1000-fold higher than the activity of vanillin alone, i.e. when not in combination with the terpenoid. As shown in Example 3, this effect is not confined only to diterpenoids, such as abietic, dehydroabietic and pimaric acid, but also extends to a range of triterpenoids, such as ursolic acid, oleonic acid and betulin. In general, antimicrobial substances are used in a pure form, and so the inventors believe that they are the first to observe that any terpenoid, such as dehydroabietic acid, has the surprising ability of enhancing the antimicrobial activity of natural or synthetic antimicrobial agents, such as vanillin.

The term "increase antimicrobial activity of the antimicrobial agent" may mean that the antimicrobial agent exhibits a higher antimicrobial activity in the presence of the terpenoid than in the absence of the terpenoid. It is thought that the surprising increase in activity may be the result of a synergistic effect where both substances interfere with microbial cell membrane integrity or with protein synthesis in a complimentary manner. Thus, the antimicrobial agent is capable of interfering either with the cell membrane integrity of a micro-organism, or with the protein synthesis (e.g. the RNA synthetic machinery) of the micro-organism, while the terpenoid may allow these agents to enter the cell more easily or enhance their function.

The antimicrobial activity of the antimicrobial agent may be increased by at least 1-fold, at least 2-fold, at least 3-fold, at least 5-fold, at least 8-fold, or at least 10-fold. Antimicrobial activity may be increased by at least 20-fold, at least 50-fold, at least 100-fold, 200-fold, 300-fold, 500-fold, 700-fold, or 1000-fold. Antimicrobial activity may even be increased by at least 1200-fold, at least 1500-fold, 1700-fold or at least 2000-fold or more. Such increases in antimicrobial activity may be determined using assays such as those that are described in the Examples.

The inventors have tested a wide variety of heated plant materials, and have found that heated wood shavings derived from various hardwoods and softwoods, for example pine wood and bark, which comprise terpenoids and antimicrobial agents exhibit surprising antimicrobial properties. Thus, the terpenoid and/or the antimicrobial agent may be derived from a plant, such as a hardwood or softwood. Examples of suitable hardwood species from which the terpenoid and/or antimicrobial agent may be derived include holly (*Ilex* genus), oak (*Quercus* genus), beech (*Fagus* genus), ash (*Fraxinus* genus), maple (*Acer* genus), poplar (*Populus* genus), willow (*Salix* genus), and chestnut (*Castanea* genus), such as sweet chestnut (*Castanea sativa*).

Suitable softwood species from which the terpenoid and/or antimicrobial agent may be obtained include a conifer or a pine tree. Examples of suitable softwoods therefore include pine (*Pinus* genus), spruce (*Picea* genus), cedar (*Cedrus* genus), fir (*Abies* genus), larch (*Larix* genus), douglas-fir (*Pseudotsuga* genus), hemlock (*Conium* genus), cypress (Cupressaceae family), redwood (*Sequoia* genus) and yew (*Taxus* genus). The inventors have found that material derived from pine, and especially Scots Pine, is surprisingly effective at exhibiting antimicrobial activity, and therefore provides a useful source for the composition of the invention. Hence, the terpenoid and/or antimicrobial agent may be derived from the Pinaceae family, and preferably the *Pinus* genus, such as *Pinus silvestrus* or *Pinus negrus*. Materials, such as rosins and disproportionated rosins that are derived from wood, are also a good source of terpenoids for use in the invention.

The plant material from which the terpenoid and/or antimicrobial agent is derived may first be heated, for example by exposure to a temperature of at least 50° C. or at least 115° C. The plant material may be exposed to a temperature of less than 200° C. or less than less than 150° C. The plant material may be exposed to a temperature of between 75° C. and 175° C. or between 100° C. and 160° C. The plant material may be exposed to the treatment temperature for at least 30 minutes, at least one hour, at least 5 hours, at least 24 hours, at least 36 hours, at least 48 hours or at least 72 hours. The inventors have found that exposure to such heat-treatment results in an antimicrobial composition of the invention.

Terpenoids, as used in the composition of the first aspect, or the use of the second aspect, consist of isoprene units, i.e. 2-methyl-1,3-butadiene or $CH_2=C(CH_3)CH=CH_2$). An isoprene unit may be represented by the general formula (I):

(I)

Terpenoids have a hydrophilic part (normally a carboxylic acid), and a hydrophobic part (normally a multi-ring structure). The terpenoid may be a resin acid. Resin acids can be protectants and wood preservatives that are produced by parenchymatous epithelial cells that surround the resin ducts in trees.

Terpenoids are classified according to the number of isoprene units. Thus, the terpenenoid may be a diterpenoid or a triterpenoid. Diterpenoids have four isoprene units, and triterpenoids have six isoprene units. A suitable triterpenoid, which may be used in the first or second aspect, may be selected from the group of triterpenoids consisting of ursolic acid, oleanolic acid, betulinic acid, moronic acid and lupeol. Triterpenoids are described in Example 3.

Diterpenoids, which include resin acids and oxidised resin acids, have a hydrophobic moiety consisting of a substituted decalin skeleton and a hydrophilic region possessing one hydrogen bond donor group. Diterpenoids are described in Examples 1 and 2. A suitable diterpenoid may be selected from the group of diterpenoids consisting of dehydroabietic acid; abietic acid; pimaric acid; kaurenoic acid; ent-3-β-hydroxykaurenoic acid; salvic acid; torarol; 18-acetoxy-cis-cleroda-3,13-Z-dien-15-oic acid; abietinol (7,13-abietadien-18-ol); dehydroabieticylguanidines; pisiferic acid; ferruginol; isopimaric acid; 7-oxo-dehydroabietic acid; 7-hydroxy-dehydroabietic acid; and 13-hydroxy-podocarpa-8,11,13-trien-18-oic acid.

Abietic acid may be represented by the general formula (II):

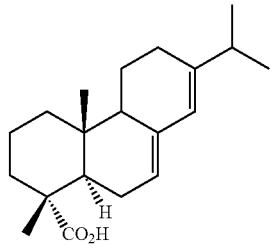

(II)

Accordingly, the terpenoid in the composition of the first aspect or the use of the second aspect may be abietic acid, or a derivative thereof.

The inventors believe that they are the first to produce a disinfectant or antiseptic composition comprising an abietic acid and an anti-microbial agent. Thus, the composition of the first aspect may be an antiseptic or a disinfectant. An antiseptic can be any antimicrobial substance that is applied to living tissue or skin to reduce or prevent a microbial infection or sepsis. It is therefore preferred that the active ingredient within the antiseptic is of a sufficient specificity and concentration that it may be applied to the skin or tissue without causing toxic effects or irritation, and yet can kill micro-organisms thereon. A disinfectant can be any antimicrobial substance which kills micro-organisms found on non-living objects or surfaces.

Suitable abietic acids, which may be used in accordance with the invention, may include neo-abietic acid, palustric acid, levopimaric acid, dehydroabietic acid, or derivatives thereof.

Preferably, therefore, the terpenoid is dehydroabietic acid (DHAA), or a derivative thereof. Dehydroabietic acid and suitable derivatives thereof may be represented by the general formulae (III), (IV) or (V):

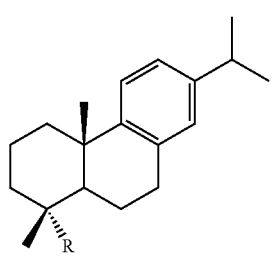

(III)

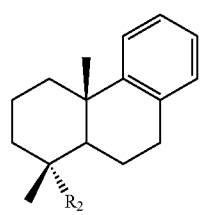

(IV)

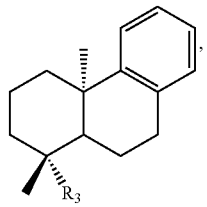

(V)

in which R is $CO_2H$, $CO_2Me$, $CH_2OH$ or CHO; $R_2$ is $CO_2H$, $CO_2Me$ or $CH_2OH$; and R3 is $CO_2H$, $CO_2Me$ or $CH_2OH$.

Terpenoids may be modified in a variety of different ways using for example dehydration, halogenation, oxidation or methylation to form a range of derivatives having characteristics described herein. Thus, suitable derivatives of the terpenoid may include dehydrated, oxidised, methylated or halogenated forms of the terpenoid. For example, abietic acid may be dehydrated to form pimaric acid. Alternatively, DHAA may be halogenated to form 12,14-dichlorodehydroabietic acid.

The terpenoid or derivative thereof may be treated with a base, for example sodium hydroxide, to form the corresponding salt (e.g. DHAA hydroxide). The salt may be easily dissolved in water to form a solution, which may be applied to a surface, for example by a spray or by immersion in the solution itself.

The antimicrobial agent used in accordance with the invention may be capable of interfering with the integrity of the cell membrane of a micro-organism. The mechanisms by which this occurs are thought to be different for different substances, but it has been suggested that a lipophilic portion in the antimicrobial agent can react with the phospholipid components of the cell membrane of the micro-organism, thereby modifying the activity of calcium and potassium ion channels situated in the membrane. Furthermore, the antimicrobial agent can interact with the cell membrane by means of its physiochemical properties and molecular shape, thus influencing the activity of membrane enzymes, membrane carrier molecules and membrane receptors. Any or all of these mechanisms can interfere with the integrity of the micro-organism's cell membrane, resulting in cell death.

Many essential oils, such as those extracted from plants, exhibit variable antimicrobial activity. Hence, in one embodiment of the invention, the antimicrobial agent used in the first or second aspect may comprise an essential oil. Suitable essential oils that may be used include Thyme oil (active ingredient: thymol), Clove oil (active ingredient: Eugenol), Tea-tree oil (active ingredient Terpinen-4-ol), Aniseed oil, Calamus oil, Camphor oil, Cedar wood oil, Cinnamon oil, Citronella oil, Lemon oil, Lemon grass oil, Lime oil, Nutmeg oil, Pamarosa oil, Peppermint oil, Rosemary oil, Basil oil, Vetiver oil, Black pepper oil, Ginger oil, Myrrh oil, Oregano oil, Bay leave oil, Geranium oil, Orange oil, Dill oil or Wintergreen oil.

Thus, the antimicrobial agent may comprise thymol, or a derivative thereof. The chemical formula and structure of thymol is provided herein.

Essential oils are believed to interact with the integrity of the microbial cell membrane in the manner described above, i.e. the lipophilic fraction in the oil reacts with the lipid part of the cell membrane, modifying the activity of ion channels in the membrane. Furthermore, essential oils are believed to interact with the cell membrane by means of their physiochemical properties and molecular shapes. Essential oils normally contain a mixture of biologically active compounds, but the main constituents, that are believed to be responsible for their antimicrobial activity, are phenols. Examples of phenolic compounds that are found in essential oils are provided in Table 1.

TABLE 1

Examples of anti-microbial phenolic compounds found in essential oils

| Name of phenolic compound | Formula | Plant in which it is found |
|---|---|---|
| Anethole | $C_{10}H_{12}O$ | Fennel |
| Borneol | $C_{10}H_{18}O$ | Citronella |
| Carvacrol | $C_{10}H_{14}O$ | Oregano |
| Cinnamol | $C_9H_8O$ | Cinnamon |
| p-Cuminol | $C_9H_{12}O$ | Cumin |
| Estragole | $C_{10}H_{12}O$ | Basil |
| Eugenol | $C_{10}H_{12}O_2$ | Clove |
| Menthol | $C_{10}H_{20}O$ | Peppermint |
| Methyl Salicylate | $C_8H_8O_3$ | Wintergreen/Birch |
| Myristicin | $C_{10}H_{10}O_3$ | Nutmeg |
| Terpinen-4-ol | $C_{10}H_{18}O$ | Tea tree |
| Thymol | $C_{10}H_{14}O$ | Thyme |

Thus, the antimicrobial agent used in accordance with the invention may extend to the use of any of the phenolic compounds listed in Table 1.

Other biologically active compounds in essential oils, which are also believed to have antimicrobial activity, include o-Cresol, m-Cresol, p-Cresol, Carvacol, Creosol, Isoeugenol, Hydroquinone, Guaiacol, Methyl salycilate, Trans-Anethole, Methyl eugenol, Methyl chavicol, p-Methoxy phenylacetone, Benzaldehyde, Anisaldehyde and Cuminaldehyde. Thus, the antimicrobial agent of the invention may also include any of these compounds.

As described in the Examples, the inventors have demonstrated that the antimicrobial activity of the agent, vanillin, is surprisingly enhanced when in combination with the terpenoid, dehydroabietic acid. Thus, the antimicrobial agent may be vanillin or a derivative thereof. It will be appreciated that vanillin (also known as methyl vanillin or 4-hydroxy-3-methoxybenzaldehyde) is an organic compound having the molecular formula $C_8H_8O_3$, and is represented by the formula VI:

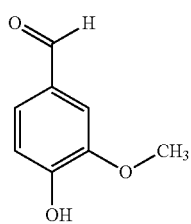

VI

Accordingly, in one embodiment, the composition of the first aspect of the invention comprises dehydroabietic acid or a derivative thereof, and vanillin or a derivative thereof. In one embodiment of the use of the second aspect, dehydroabietic acid or a derivative thereof is used to elevate the antimicrobial characteristics of vanillin or a derivative thereof.

A common derivative of vanillin is vanillic acid, which is represented by the formula VII:

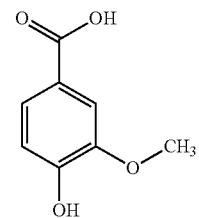

VII

Another suitable derivative of vanillin may include ethyl vanillin.

As shown in FIG. 2, the inventors have demonstrated that the antimicrobial activity of stilbene can also be surprisingly augmented by a terpenoid, such as DHAA. Thus, in another embodiment, the antimicrobial agent may be stilbene, or a derivative thereof. Two possible isomers of stilbene exist, the cis- and the trans-isomer, which are represented by formulae VIII and IX:

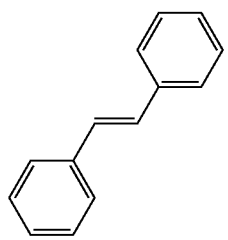

VIII

IX

As described in Example 12, the inventors have demonstrated that the antimicrobial activity of coniferaldehyde can also be surprisingly augmented by a terpenoid, such as DHAA. Therefore, in another embodiment, the antimicrobial agent may be coniferaldehyde or a derivative thereof, which is represented by formula X:

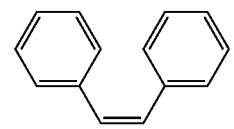

X

As described in Example 8, the inventors have demonstrated that the antimicrobial activity of dehydrozingerone can also be surprisingly augmented by a terpenoid, such as DHAA. Hence, in yet another embodiment, the antimicrobial agent may be dehydrozingerone or a derivative thereof, which is represented by formula XI:

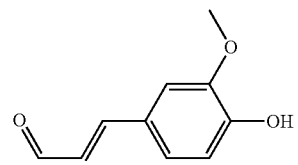

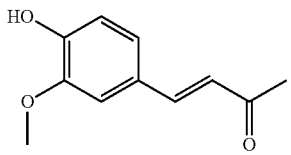

Hence, in another embodiment, the composition of the first aspect of the invention may comprise dehydroabietic acid or a derivative thereof, vanillin or a derivative thereof and/or stilbene and/or coniferaldehyde and/or dehydrozingerone, or derivatives thereof.

Furthermore, in another embodiment, the use of the second aspect may comprise dehydroabietic acid and/or stilbene and/or coniferaldehyde and/or dehydrozingerone, or derivatives thereof for elevating the antimicrobial characteristics of vanillin, or a derivative thereof.

In yet another embodiment, the antimicrobial agent may be proteinaceous, and preferably comprises at least one polypeptide. As a result, the agent may be digested by protease enzymes upon consumption by a subject. For example, the antimicrobial agent may be nisin, which is a polycyclic peptide antibacterial compound having 34 amino acids. Upon consumption by a subject, nisin is rapidly inactivated by proteases present in the subject. As described in Example 5, the inventors have demonstrated that dehydroabietic acid is poorly soluble in water and that, surprisingly, water extracts from materials that contain both dehydroabietic acid and vanillin are non-toxic to microbial cells. Instead, the antimicrobial activity remains with the treated material. Therefore, combining dehydroabietic acid with a proteinaceous antimicrobial agent such as nisin would make an extremely safe product, because, not only does the dehydroabietic acid not solubilise easily, but together with a denatured protein, it would not have any toxic effect on the subject.

In addition to the aforementioned 'natural products', which may be used as antimicrobial agents in accordance with the invention, there is a wide range of chemicals that are also capable of disrupting microbial cell membranes, and which cause the death of micro-organisms, and which can therefore also be used as antimicrobial agents in accordance with the invention. These compounds may be categorised into alcohols, aldehydes, oxidising agents, phenolics or quaternary ammonium compounds. Normally, such compounds are used for cleaning surfaces and in water supplies (e.g. chlorine). Accordingly, increasing their antimicrobial activity in combination with a terpenoid such as dehydroabietic acid allows these compounds to be more effective, even when diluted. The antimicrobial agent may or may not be an antibiotic. The antimicrobial agent may or may not be a heavy metal, such as zinc.

The inventors have also found that other molecules, besides terpenoids, having a polar, acidic group or moiety and a rigid hydrophobic moiety, may also be used to increase the antimicrobial activity of antimicrobial agents, such as vanillin.

Thus, according to a third aspect of the invention, there is provided the use of a compound having a polar part and a rigid hydrophobic moiety, for increasing the antimicrobial activity of an essential oil or vanillin, or a derivative thereof.

The polar part may comprise a hydroxyl group, for example a carboxylic acid moiety. The hydrophobic moiety may comprise at least one aromatic ring, preferably a plurality of aromatic rings. The compound may be an isoflavanoid phyto-alexin (e.g. phaseolin), glyceollin or pterocarpan. The essential oil may be any one of those already described herein, or an active component thereof. It will be appreciated that the use of the third aspect may be applied to any of the applications described in any of the following aspects of the invention.

The inventors have carefully considered the chemical structures of each of the antimicrobial agents described herein, which may be used in accordance with the invention, and have found that they may all be represented by the same chemical formula.

Hence, the antimicrobial agent may be represented by formula XII:

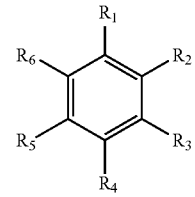

XII wherein $R_1$, $R_2$, $R_3$, $R_4$, $R_5$ and $R_6$ is independently selected from a group consisting of H; OH; $C_1$-$C_4$ alkyl or alkylene; $C_1$-$C_4$ alkoxy; $C_1$-$C_4$ saturated or unsaturated aldehyde; $C_2$-$C_4$ ester or ketone; $C_1$-$C_4$ carboxyl; and $C_1$-$C_3$ alkyl-substituted phenyl group.

$R_1$ may be OH, $C_1$-$C_4$ alkyl or alkoxy, $C_1$-$C_4$ aldehyde, or a $C_1$-$C_2$, alkyl substituted phenyl group. $R_1$ may be OH, $C_1$ alkoxy, $C_1$ aldehyde, or a $C_1$-$C_2$ alkyl substituted phenyl group.

$R_2$ may be H, $C_1$-$C_4$ alkyl or alkoxy, or $C_2$-$C_4$ ester. $R_2$ may be H, $C_1$-$C_3$ alkyl, $C_1$-$C_3$ or alkoxy, or $C_2$-$C_3$ ester.

$R_3$ may be H, or $C_1$-$C_4$ alkyl. $R_3$ may be H, or $C_1$-$C_3$ alkyl.

$R_4$ may be H, $C_1$-$C_4$ alkyl or alkylene, $C_1$-$C_4$ alkoxy, $C_1$-$C_4$ saturated or unsaturated aldehyde, or $C_2$-$C_4$ ketone. $R_4$ may be H, $C_1$-$C_3$ alkyl or alkylene, $C_1$-$C_2$ alkoxy, $C_1$-$C_2$ saturated or unsaturated aldehyde, or $C_2$-$C_3$ ketone.

$R_5$ may be H, or $C_1$-$C_4$ alkyl. $R_5$ may be H, or $C_1$-$C_2$ alkyl.

$R_6$ may be H, or $C_1$-$C_4$ alkyl. $R_6$ may be H, or $C_1$-$C_2$ alkyl.

$R_1$, $R_2$, $R_3$, $R_4$, $R_5$ and $R_6$ may be as defined in the table below.

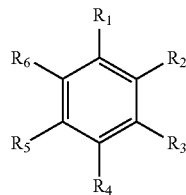

Compound (XII)

| | $R_1$ | $R_2$ | $R_3$ | $R_4$ | $R_5$ | $R_6$ |
|---|---|---|---|---|---|---|
| Phenol | —OH | —H | —H | —H | —H | —H |
| o-Cresol | —OH | —CH$_3$ | —H | —H | —H | —H |

Compound (XII)

| | $R_1$ | $R_2$ | $R_3$ | $R_4$ | $R_5$ | $R_6$ |
|---|---|---|---|---|---|---|
| m-Cresol | —OH | —H | —CH3 | —H | —H | —H |
| p-Cresol | —OH | —H | —H | —CH$_3$ | —H | —H |
| Thymol | —OH | -i-Pr | —H | —H | —CH$_3$ | —H |
| Carvacol | —OH | —H | -i-Pr | —H | —H | —CH$_3$ |
| Creosol | —OH | —OCH$_3$ | —H | —CH$_3$ | —H | —H |
| Isoeugenol | —OH | —OCH$_3$ | —H | -cis, trans-1-propenyl | —H | —H |
| Eugenol | —OH | —OCH$_3$ | —H | -2-propenyl | —H | —H |
| Coniferaldehyde | —OH | —OCH$_3$ | —H | -propenal | —H | —H |
| Hydroquinone | —OH | —H | —H | —OH | —H | —H |
| Vanillin | —OH | —OCH$_3$ | —H | —CHO | —H | —H |
| Ethyl vanillin | —OH | —OCH$_2$CH$_3$ | —H | —CHO | —H | —H |
| Guaiacol | —OH | —OCH$_3$ | —H | —H | —H | —H |
| Methyl salycilate | —OH | —COOCH$_3$ | —H | —H | —H | —H |
| Trans-Anethole | —OCH$_3$ | —H | —H | -trans-1-propenyl | —H | —H |
| Methyl eugenol | —OCH$_3$ | —OCH$_3$ | —H | -2-propenyl | —H | —H |
| Methyl chavicol | —OCH$_3$ | —H | —H | -2-propenyl | —H | —H |
| p-Methoxy phenylacetone | —OCH$_3$ | —H | —H | -ketopropyl | —H | —H |
| Benzaldehyde | —CHO | —H | —H | —H | —H | —H |
| Anisaldehyde | —CHO | —H | —H | —OCH$_3$ | —H | —H |
| Cuminaldehyde | —CHO | —H | —H | -i-Pr | —H | —H |
| Vanillic acid | —OH | —OCH$_3$ | —H | —COOH | —H | —H |
| Dehydrozingerone | —OH | —OCH$_3$ | —H | C$_2$H$_2$COCH$_3$ | —H | —H |
| Stilbene | C$_2$H$_2$C$_6$H$_5$ | —H | —H | —H | —H | —H |

It will be appreciated that there are many components of oxygenated essential oils or derivatives thereof that can have the above general formula XII, but which are not specifically mentioned in the list.

In a fourth aspect, there is provided an antimicrobial composition comprising a terpenoid or a derivative thereof, and an antimicrobial agent represented by formula XII:

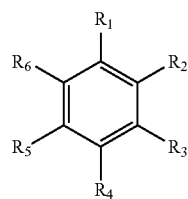

XII wherein $R_1$, $R_2$, $R_3$, $R_4$, $R_5$ and $R_6$ is independently selected from a group consisting of H; OH; $C_1$-$C_4$ alkyl or alkylene; $C_1$-$C_4$ alkoxy; $C_1$-$C_4$ saturated or unsaturated aldehyde; $C_2$-$C_4$ ester or ketone; $C_1$-$C_4$ carboxyl; and $C_1$-$C_3$ alkyl-substituted phenyl group.

In a fifth aspect, there is provided use of a terpenoid or a derivative thereof for increasing the antimicrobial activity of an antimicrobial agent represented by formula XII:

XII wherein $R_1$, $R_2$, $R_3$, $R_4$, $R_5$ and $R_6$ is independently selected from a group consisting of H; OH; $C_1$-$C_4$ alkyl or alkylene; $C_1$-$C_4$ alkoxy; $C_1$-$C_4$ saturated or unsaturated aldehyde; $C_2$-$C_4$ ester or ketone; $C_1$-$C_4$ carboxyl; and $C_1$-$C_3$ alkyl-substituted phenyl group.

The antimicrobial compositions according to the invention may be used to prevent, combat or treat any microbial infection, be it bacterial or fungal. A bacterial infection which may be treated or prevented with the antimicrobial composition of the first or fourth aspects may be a Gram-positive or a Gram-negative bacterial infection. Examples of Gram-positive bacteria, which the composition may be used to combat, include those in the phylum Firmicutes, which includes *Bacillus* spp., *Clostridium* spp., *Mycobacterium* spp., *Staphylococcus* spp., *Streptococcus* spp. and *Enterococcus* spp. For example, the Gram-positive bacteria may be *S. aureus*. Examples of Gram-negative bacteria, which the composition may be used to combat, include Enterobaceriaceae, such as *Salmonella* spp. (such as *Salmonella enterica, S. enteritidis* or *S. typhimurium*), and *Escherichia* spp. (such as *E. coli*). *Campylobacter* spp. and *Pseudomonas* spp. are other examples of Gram-negative bacteria which may be treated with the composition of the invention.

Examples of fungal infections that affect humans or animals, and which the composition may be used to combat, are mainly dermatological. For example, the fungus which may be combated may be a filamentous fungus, such as *Penicillium* spp. or *Aspergillus* spp. Examples of mycosis that affect the skin are Tinea versicolor (causal agent *Pityrossporum orbiculare*), ringworm, athlete's foot and tinea (causal agents are fungi of the genera *Microsporum, Trichophyton* and *Epidermophyton*) as well as yeast infections such as thrush (Causal agent *Candida albicans*). Also, fungal infections of the scalp that cause flaking of the skin (dandruff) can be treated with the compositions of the invention. Besides fungal infections that affect mammals, the compositions of the invention may be used to combat fungal infections of plants or plant products. Of particular interest are fungi that survive on plant residues or sporulate even when the plant itself is killed. Examples of fungal diseases that survive on dead plant material and which cause significant damage include fungi of the genera, *Phytophthora, Pythium, Sclerotinia, Verticillium, Ventura, Botrytis* and *Fusarium*. One example of a particularly damaging disease is *Phytophthora ramorum*, the causal agent of Sudden Oak Death. This disease infects Rhododendron species and can be devastating for oak (*Quercus*). The compositions of the invention may also be used to combat yeast infections, such as *S. cerevisiae*.

Given the wide range of micro-organisms that may be combated with compositions of the invention, the inventors believe that the composition of the first or fourth aspects can be applied to a wide range of antimicrobial uses (whether in a clinical context or otherwise), such as in industrial, domestic, healthcare, packaging and engineering applications in which microbial activity or even presence is a problem, by increasing the activity of known antimicrobial agents. Preferably, the composition is applied in a soluble form (i.e. dissolved in an alcohol or acetone) or by transforming it into a salt which would make it water soluble. However, when not in the form of a salt, once the solute has evaporated, the composition presents itself as a water insoluble form, i.e. absorbed, integrated or coated onto a support surface or material.

Therefore, in a sixth aspect of the invention, there is provided a liquid formulation comprising the antimicrobial composition of the first or fourth aspect.

Natural compounds with low mammalian toxicity, a pleasant or no taste or smell at all, and with good and wide-ranging antimicrobial properties have many applications. For example, they may be used to sanitise animal bedding and animal beds, or to sanitise surfaces, for example those that are used for food preparation. Compositions may also be used in antiseptic hand washes and soaps, anti-dandruff shampoos, dermatological creams and in mouthwashes.

Advantageously, the use of a terpenoid to improve the activity of an antimicrobial agent, which interferes with cell membrane integrity, such as vanillin or an essential oil, results in the significant enhancement of the activity of existing natural products even when the original active ingredient is at a low concentration (i.e. very diluted). Therefore, the composition of the first or fourth aspect is effective at low concentrations such that it does not smell or have a taste. Furthermore, it is important that the composition of the invention is non-hazardous to humans or mammals, and because the compounds are naturally ubiquitous in the environment, there is no significant added impact on the environment when treated products are disposed of via normal waste disposal routes.

In one embodiment, the antimicrobial composition may be used to treat animal bedding, as its antimicrobial properties prevent the growth of *Salmonella, Campylobacter, Mycobacterium* and *E. coli*, which are all major animal pathogens known to be associated with animal bedding. Inhibition of a wide variety of micro-organisms involved in the conversion of uric acid and urea to ammonia prevents animal beddings becoming caustic and prevents the release of ammonia into the atmosphere.

Hence, in a seventh aspect there is provided animal bedding comprising the antimicrobial composition according to the first or fourth aspect.

To effectively reduce ammonia formation and the number of pathogens in the animal bedding of the fifth aspect, wood shavings or other adsorbents such as paper, perlite or another porous material is treated with the composition of the first aspect. It is preferred that the composition comprises dehydroabietic acid or a derivative thereof in combination with vanillin. The composition may comprise an alcohol or acetone as solvent. Hence, the bedding material may be treated by direct spraying, or by immersing or mixing the solution with the bedding material, and then allowing the solvent to evaporate. Alternatively, the composition is first made water-soluble by formation of a salt allowing it to be formulated with water or other polar solutes.

Advantageously, the bedding of the seventh aspect reduces odours, and increases animal welfare. The animal bedding may be used in the animal rearing industry, for example in poultry, such as of chickens, turkeys, ducks, foul or geese, but also as an animal bedding for pigs, cattle, sheep, horses and other animals. Alternatively, the animal bedding may be used in the pet industry, for example for bedding of rabbits, guinea pigs, hamsters, gerbils, rats, mice or caged birds. The bedding of the seventh aspect may also be used for animals used in animal laboratory testing, such as mice, rats or rabbits (e.g. for knockout/nude mice). The bedding may also be used as animal bedding/litter in husbandry of animals in zoos. The bedding may also be used as animal bedding for the transportation of live animals, or for use as animal bedding/litter for egg laying hens, as *Salmonella enteritidis* is known to infect the ovaries of healthy hens and contaminates the eggs before the shells are formed.

The composition of the first or fourth aspect may also be used in horticulture and Silviculture to prevent crop losses from plant diseases caused by fungal or bacterial infections. Hence, the composition may be used as a mulch, i.e. a protective cover over soil that prevents soil-borne pathogens from infecting plants, fruits or vegetables. Alternatively, the composition may be directly applied to plant residues to prevent pathogens colonising these materials from spreading.

Hence, in an eighth aspect, there is provided a mulch comprising the antimicrobial composition according to the first or fourth aspect.

The mulch may be used to minimise or prevent loss of crops due to microbial infection. For example, 50% of strawberries and 20-40% of grapes are lost to fungal infections, such as *Botrytis*, and 70% of the monetary value of apples can be lost to apple scab. It is believed that such crop losses may be avoided by using the mulch.

The inventors also believe that the composition of the first or fourth aspect can be applied for the prevention or inhibition of microbial colonisation of an object per se.

Thus, in a ninth aspect, there is provided a method of preventing or inhibiting microbial colonisation of an object, which method comprises contacting or coating a surface of the object with the antimicrobial composition of the first or fourth aspect.

Hospital "superbugs" are one of the major problems in the health system, and antimicrobial products could be an effective solution to overcome the problem. The compositions of the invention have been shown to be effective in the prevention of growth of Gram-positive bacteria, such as *Staphylococcus aureus* and *Clostridium difficile*. The technology also can be applied to natural (i.e wool, cotton, linen, jute, etc) and artificial fibres such as those made from nylon and polyester, which can be used to make patient clothing, and bedding products. Other applications include the treatment of medical equipment, furniture, electrical and electronic products, and window frames.

In a tenth aspect, there is provided an object comprising the antimicrobial composition according to the first or fourth aspect.

The object may be coated with the composition. Preferably, once applied, the composition is in an insoluble form. Preferably, the amount of composition that is used in the method of the ninth aspect or the object of the tenth aspect is sufficient to be effective for killing or preventing growth of micro-organisms. It will be appreciated that the compositions of the invention may be particularly useful for coating surfaces or objects that are required to be aseptic, and as discussed above, the compositions have the advantage that they are antimicrobial for prolonged periods of time. The compositions of the invention may be used to coat any object or device used in a biological or medical situation or environment, for which it may be important to prevent microbial infection or contamination that may lead to infection in a patient on a long term basis.

The object may be a medical device. Examples of medical devices that may be coated using the compositions of the invention include catheters, stents, wound dressings, bandages, contraceptive devices, surgical implants and replacement joints, contact lenses etc. The compositions of the invention are particularly useful for coating biomaterials and objects and devices made therefrom. Microbial contamination/colonisation of biomaterials can be particularly problematic because the micro-organism may use such material as a substrate for growth. Biomaterials (eg. collagens and other biological polymers) may be used to cover the surface of artificial joints. Alternatively, certain implants may substantially comprise such biomaterials which comprise the disinfectant of the invention.

Creating an effective barrier for infectious agents is an important consideration when developing bandages, wound dressings and plasters. Therefore, treating such products with the compositions of the invention allows the exchange of gases, while creating a barrier for pathogenic organisms. Similarly, bed linen can be treated with the composition to render it antimicrobial.

The compositions of the invention may be used to coat any surfaces in environments that are required to be aseptic, such as medical environments. The compositions may be used to keep hospital wards clean, and so almost any parts of a hospital may be coated with the compositions of the invention. The compositions may be used to prevent infection on surfaces of medical equipment (e.g. operating tables) in operating theatres, as well as theatre walls and floors, and so these may be coated with the compositions of the invention. The inventors believe the compositions described herein will be very useful to improve sterility and cleanliness in general.

The compositions of the invention may also be used to protect a wide range of domestic products, which may be prone to microbial infection. The product may be coated with the composition, and may be any of a wide range of different product types, e.g. a food preparation surface, a kitchen chopping board or a carpet. Carpets are normally made from wool, nylon, polyester and polypropylene fibres, and which could simply be coated with the compositions of the invention. However, it will be appreciated that the potential applications could be much wider. The above list of objects and surfaces to which the compositions according to the invention may be applied is not exhaustive. Hence, the compositions may be applied administered to any surface prone to microbial infection or contamination, for example kitchen and bathroom surfaces and products, such as a toilet seat, or the toilet itself.

The inventors envisage that the compositions of the invention may be used in the manufacture of antimicrobial materials such as, insoles for shoes that are made from a polymer, textiles or fabrics, which may be used to make bedding, and are also used in the clothing and fashion sectors.

Accordingly, in an eleventh aspect, there is provided a polymer or textile comprising the antimicrobial composition according to the first or fourth aspect.

The textile of polymer may have applications, for example in bedding used in hospitals and operating theatres, e.g. pillow covers, bed sheets, and duvet covers. The textile or polymer may be used in the manufacture of clothing, for example clothing prone to microbial infection, such as underwear or an insole for footwear.

Therefore, in a twelfth aspect, there is provided a clothing article comprising the textile or polymer according to the eleventh aspect.

The clothing article may be an article of underwear or the insole of a shoe. The clothing article may be footwear.

Thus, in a thirteenth aspect, there is provided footwear or an insole therefor comprising the textile or polymer according to the eleventh aspect.

The antimicrobial compositions of the invention may also be used in defence applications. Soldiers, particularly those in combat, suffer from hygiene concerns as they are unable to wash frequently, and are therefore prone to microbial infection. Hence, the clothing article of the twelfth aspect may be a uniform, and preferably a military uniform.

Other applications of the invention involve food packaging. After fruit has been harvested, crop losses due to fungal and bacterial infections are common, and it is estimated that post harvest losses at least equal pre-harvest losses. Hence, there is a significant need for antimicrobial materials which can be used in the food packaging industry.

Hence, in a fourteenth aspect, there is provided a packaging material comprising the antimicrobial composition according to the first or fourth aspect.

Preferably, the packaging material is used for the packaging of perishable products, i.e. any product having limited lifespan or one which is at risk of microbial infection. Preferably, the packaging material is used for packaging a food product or foodstuff. The packaging material may prevent losses to perishable or freshly harvested food products, such as fruits and vegetables, which are susceptible to infection by spoilage organisms, such as fungi and bacteria. To prevent losses caused by these spoilage organisms, the packaging material may be coated or sprayed with, or dipped in, the composition of the first or fourth aspect.

The food product which may be packaged with the packaging material may be a fruit (e.g. nectarines, peaches, apples or pears) or a vegetable, meat, bread, or biscuits etc. Fruit is used herein as an example of produce that is highly susceptible to post-harvest diseases, but other agricultural products such as potatoes, carrots, lettuce etc, could benefit from being protected by the compositions of this invention.

In a fifteenth aspect, there is provided use of the antimicrobial composition of the first or fourth aspect, for use in a method of preventing or inhibiting microbial infection of a food product, which method comprises contacting or coating a surface of a food product with the antimicrobial composition of the first or fourth aspect.

The food product may be a fruit, vegetable, meat, or diary product. Essential oils are frequently used in fruit packaging, because, due to their volatile nature, they create an atmosphere that inhibits food spoilage organisms. Once the food product is unpacked, the essential oils evaporate and do not leave any residues on the food product. The inventors therefore envisage use of the composition of the first or fourth aspect, in which the terpenoid, is combined with an essential oil to treat food products, such as fruit. Use of terpenoids in combination with an antimicrobial agent, which interferes with cell membrane integrity, such as an essential oil, results in a much greater antimicrobial effect. When the fruit is unpacked, the essential oils evaporate leaving no essential oil residue, while the remaining molecule per se is not harmful. Thus, the treatment is not harmful to humans who would eat the fruit.

Application of for example, dehydroabietic acid, together with a natural antimicrobial agent is on the surface of the food product, such as a piece of fruit. Because only the surface of the fruit is treated, even when the concentration per unit surface area is high, the concentration per unit weight or volume will be low, depending on the size of the fruit. Furthermore, ingestion of the fruit will result in a further dilution of the composition as a result of the food being mixed with saliva and digestive juices in the gut. It is known that dehydroabietic acid and other terpenoids are poorly soluble in water, and it can therefore be assumed that it will have little effect when ingested, even when applied with a substance that affects cell membrane integrity.

Furthermore, in Example 5, the inventors tested the antimicrobial properties of water extracts of heated pine shavings (which contain both dehydroabietic acid and a range of antimicrobial products, including vanillin). Each of these extracts showed very little effect on *Salmonella*, while the shavings themselves remained highly antimicrobial after extraction. This clearly demonstrates that dehydroabietic acid is poorly soluble in water, and is therefore unlikely to cause any toxic effect when ingested. To make the composition even safer, it is preferred that the terpenoid is combined with an antimicrobial agent that is rapidly degraded in the stomach, for example a proteinaceous compound, such as nisin.

The inventors also envisage using the composition of the first or fourth aspect for treating or coating a receptacle or container.

Hence, in a sixteenth aspect, there is provided a container comprising the antimicrobial composition according to the first or fourth aspect.

The container may be capable of storing food, i.e. a food container. The container may be capable of storing any food material which may be prone to rotting, wastage or microbial infection, such as fresh food or produce. For example, the food may comprise fruit or vegetables. The composition of the first or fourth aspect may also be used for treating receptacles for waste material, or as an additive to waste material containers. Hence, the container may be capable of containing waste, i.e. a waste container. The container may be used to store any potentially degradable waste material, such as food waste. Degradable waste, such as organic kitchen waste, attracts flies and generates bad odours when not treated properly. Hence, the waste container treated with the composition may be a household or commercial waste bin which results in the reduction or elimination of flies or odour.

In summary, the compositions of the invention comprise a terpenoid in combination with an antimicrobial agent, which interferes with the integrity of the microbial cell membrane, or protein synthesis, such as RNA synthesis. It will be appreciated that most synthetic antimicrobial agents (such as phenols, alcohols, chlorinated compounds, etc) are highly soluble, and are therefore toxic to human cells upon exposure. Essential oils tend to be more hydrophobic, but are only mildly antimicrobial. However, as described in Example 5, dehydroabietic acid is poorly soluble in water, thereby limiting its effect to only the specific surfaces that are treated. This is a clear advantage as its application to animal bedding, hospital and domestic surfaces and foodstuffs, for example, in any of the applications described above, will not lead to transfer of the substance to humans contacting the treated object. Therefore, the treated objects are rendered antimicrobial, yet are non-hazardous to animals and humans. Furthermore, the use of a terpenoid such as dehydroabietic acid in combination with mildly antimicrobial natural products (such as essential oils) allows these products, which are normally expensive with strong tastes and smells, to be used with high efficacy at vastly reduced concentrations.

In a further aspect, there is provided an antimicrobial composition comprising a terpenoid or a derivative thereof, and an antimicrobial agent, which agent interferes with cell membrane integrity.

In a further aspect, there is provided use of a terpenoid or a derivative thereof for increasing the antimicrobial activity of an antimicrobial agent, which agent interferes with cell membrane integrity.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made to the following Figures and Examples.

FIG. 1 shows an inhibition experiment using one embodiment of the composition of the invention, comprising a combination of vanillin and DHAA against *S. aureus* (Gram-positive);

FIG. 2 shows an inhibition experiment using a composition comprising a combination of stilbene and DHAA against *S. aureus;*

FIG. 3 shows an inhibition experiment using a composition comprising a combination of vanillin and DHAA against *S. enteritidis* (Gram-negative);

FIG. 4 shows an inhibition experiment using a composition comprising a combination of vanillin and DHAA against *S. typhimurium* (Gram-negative);

FIG. 5 shows an inhibition experiment using a composition comprising a combination of vanillin and DHAA against *E. coli* (Gram-negative);

FIG. 6 shows an inhibition experiment using a composition comprising a combination of vanillin and DHAA against *Penicillium* spp. (filamentous fungi);

FIG. 7 shows an inhibition experiment using a composition comprising a combination of vanillin and DHAA against *Aspergillus* V. (filamentous fungi); and FIG. 8 shows an inhibition experiment using a composition comprising a combination of vanillin and DHAA against *S. cerevisiae* (yeast).

EXAMPLES

The inventors investigated the mechanisms by which mildly heated pine shavings become antimicrobial. As described in the Examples below, they observed that the terpenoid, dehydroabietic acid, can significantly enhance the antimicrobial activity of vanillin and other natural antimicrobial agents, such as essential oils.

Example 1—Synergistic Effect of Dehydro-Abietic Acid on the Antimicrobial Activity of Vanillin The aim of this example was to determine to what extent dehydro-abietic acid increases the antimicrobial activity of vanillin.

Methodology

A 2 fold dilution series of 20 mmol of vanillin was prepared in ethanol and water (80/20 v/v) giving concentrations from 20 mmol-0.00975 mmol. A 20 mmol solution of dehydroabietic acid in alcohol and water was also prepared.

To compare the effect of dehydroabietic acid on the anti-microbial effect of vanillin, 10 µl of each vanillin dilution was pipetted onto three, 10 mg pieces of perlite, thus giving the same concentration per g perlite as was in the solution together with 10 µl of 20 mmol dehydroabietic acid. One set of control treatments did not receive dehydroabietic acid, another only 20 mmol dehydroabietic acid, and a third control treatment received neither vanillin nor dehydroabietic acid, only 10 µl alcohol and water at a ratio of 80/20. Once the alcohol had evaporated, all replicates received 10 µl of a suspension of *Salmonella enterica* containing approx $5 \times 10^6$ colony forming units (cfu) per ml giving a bacterial load of approx. $5 \times 10^4$ bacteria per perlite particle. Each perlite particle was incubated in an Eppendorf tube at 25° C. for 24 hours before each particle was dispersed in 1 ml of 0.25 strength Ringer's Solution. From each suspension, six 20 µl droplets were placed onto XLD agar each containing approximately 1000 bacterial cells.

Results

The results are shown in Table 2.

TABLE 2

Effect of vanillin and a combination of vanillin and dehydro-abietic acid on the survival of *Salmonella enterica* (n = 3)

| Conc. of Dehydro-Abietic acid (mmol) | Conc. of Vanillin (mmmol) | Average no of cfu recovered per droplet |
|---|---|---|
| 20 | 20 | 0 |
| 20 | 10 | 0 |
| 20 | 5 | 0 |
| 20 | 2.5 | 0 |
| 20 | 1.25 | 0 |
| 20 | 0.625 | 0 |
| 20 | 0.313 | 0 |
| 20 | 0.156 | 0 |
| 20 | 0.078 | 0 |
| 20 | 0.039 | 0 |
| 20 | 0.019 | 30.6 ± 0.7 |
| 20 | 0.001 | >100 |
| 20 | 0 | >100 |
| 0 | 20 | >100 |
| 0 | 10 | >100 |
| 0 | 5 | >100 |
| 0 | 2.5 | >100 |
| 0 | 1.25 | >100 |
| 0 | 0.625 | >100 |
| 0 | 0.313 | >100 |
| 0 | 0.156 | >100 |
| 0 | 0.078 | >100 |
| 0 | 0.039 | >100 |
| 0 | 0.019 | >100 |
| 0 | 0.001 | >100 |
| 0 | 0 | >100 |

Conclusions

The results presented in Table 2 show that:

(i) Vanillin on its own, at concentrations of 20 mmol or less, had no inhibitory effect on *Salmonella*;

(ii) In combination with dehydro-abietic acid, the inhibitory effect of vanillin was still significant at a concentration of 0.019 mmol. This indicates that dehydro-abietic acid increases the antimicrobial effect of vanillin at least 1000-2000 fold; and (iii) Dehydro-abietic acid at a concentration of 20 mmol had no significant anti-microbial activity.

Example 2—Effect of an Organic Acid on the Anti-Microbial Activity of Vanillin

The aim of this example was to assess if the synergistic effect of dehydro-abietic acid on vanillin was specifically related to dehydro-abietic acid, or if it could be explained by a pH effect of the acid.

Methodology

A 2 fold dilution series of 20 mmol of vanillin was prepared in ethanol and water (80/20 v/v) giving concentrations from 20 mmol-0.078 mmol. A 20 mmol solution of citric acid in water was also prepared.

To evaluate if citric acid had the same effect as dehydro-abietic acid (as described in Example 1), 10 µl of each vanillin dilution was pipetted onto three, 10 mg pieces of perlite, thus giving the same concentration per g perlite as was in the solution. Subsequently, 10 µl of 20 mmol citric acid was pipetted onto each perlite particle. One set of control treatments did not receive citric acid, the other control received neither vanillin nor citric acid, only 10 µl alcohol and water at a ratio 80/20. Once the alcohol had evaporated, all replicates received 10 µl of a suspension of *Salmonella* containing approx $5 \times 10^6$ cfu per ml giving a bacterial load of approx. $5 \times 10^4$ bacteria per perlite particle.

Each perlite particle was incubated in an Eppendorf tube at 25° C. for 24 hours before each particle was dispersed in 1 ml of 0.25 strength Ringer's Solution. From each suspension, six 20 μl droplets were placed onto XLD agar each containing approx 1000 bacterial cells.

Results

The results are show in Table 3.

TABLE 3

Effect of a combination of vanillin and citric acid on the survival of *Salmonella enterica* (n = 3)

| Conc. of citric acid (mmol) | Conc. Of Vanillin (mmol) | Average no. of cfu recovered per droplet |
|---|---|---|
| 20 | 20 | 63.7 ± 3.3 |
| 20 | 10 | >100 |
| 20 | 5 | >100 |
| 20 | 2.5 | >100 |
| 20 | 1.25 | >100 |
| 20 | 0.625 | >100 |
| 20 | 0.313 | >100 |
| 20 | 0.156 | >100 |
| 20 | 0.078 | >100 |
| 20 | 0 | >100 |
| 0 | 20 | >100 |
| 0 | 0 | >100 |

Conclusions

The results presented in Table 3 show that:

(i) Citric acid increased the effect of vanillin very slightly (2 fold maximum); and (ii) The effect of dehydro-abietic acid on the activity of vanillin cannot be attributed to a pH effect.

Example 3—Antimicrobial Activity of Vanillin in Combination with a Range of Triterpenoids The aim of Example 3 was to determine if triterpenoids, which also have a hydrophilic part and a hydrophobic part, have a similar activity as the diterpenoid, dehydroabietic acid, in relation to vanillin.

Methodology

A 10 fold dilution series of 20 mmol of vanillin was prepared in ethanol and water (80/20 v/v) giving concentrations from 20 mmol-0.02 mmol. 20 mmol solutions of ursolic acid, oleonic acid and betulin in alcohol were also prepared.

To determine the effect of ursolic acid, oleonic acid and betulin dehydroabietic acid on the anti-microbial effect of vanillin, 10 μl of each vanillin dilution was pipetted onto three, 10 mg pieces of perlite, thus giving the same concentration per g perlite as was in the solution together with 10 μl of 20 mmol of each of the triterpenoids. One set of control treatments did not receive triterpenoids, and another only 20 mmol dehydroabietic acid. Once the alcohol had evaporated, all replicates received 10 μl of a suspension of *Salmonella enterica* containing approx $5 \times 10^6$ colony forming units (cfu) per ml giving a bacterial load of approx. $5 \times 10^4$ bacteria per perlite particle. Each perlite particle was incubated in an Eppendorf tube at 25° C. for 24 hours before each particle was dispersed in 1 ml of 0.25 strength Ringer's solution. From each suspension, six 20 μl droplets were placed onto XLD agar each containing approximately 1000 bacterial cells.

Results

The results are shown in Table 4.

TABLE 4

Effect of a combination of vanillin and three triterpenoids (ursolic acid (a), oleanolic acid (b) and betulin (c)) on the survival of *Salmonella enterica* (n = 3)

(a) Ursolic acid

| Conc. of ursolic acid (mmol) | Conc. Of Vanillin (mmol) | Average no. of cfu recovered per droplet |
|---|---|---|
| 20 | 20 | 0 |
| 20 | 2 | >100 |
| 20 | 0.2 | >100 |
| 20 | 0.02 | >100 |
| 20 | 0 | >100 |
| 0 | 0 | >100 |
| 0 | 20 | >100 |

(b) Oleanic acid

| Conc. Of oleanic acid (mmol) | Conc. Of Vanillin (mmol) | Average no. of cfu recovered per droplet |
|---|---|---|
| 20 | 20 | 0 |
| 20 | 2 | 50 |
| 20 | 0.2 | >100 |
| 20 | 0.02 | >100 |
| 20 | 0 | >100 |
| 0 | 0 | >100 |
| 0 | 20 | >100 |

(c) Betulin

| Conc. Of betulin (mmol) | Conc. Of Vanillin (mmol) | Average no. of cfu recovered per droplet |
|---|---|---|
| 20 | 20 | 0 |
| 20 | 2 | >100 |
| 20 | 0.2 | >100 |
| 20 | 0.02 | >100 |
| 20 | 0 | >100 |
| 0 | 0 | >100 |
| 0 | 20 | >100 |

Conclusions

The results presented in Table 4 show that:

(i) All triterpenoids tested increased the activity of vanillin, (ii) There was no significant difference in the increase in anti-microbial effect between the three triterpenoids, and (iii) The synergistic effect of triterpenoids in conjunction with vanillin was less than that observed with the combined use of dehydroabietic acid and vanillin. The most likely reason for this is that triterpenoids are very insoluble and may not be taken up in sufficient quantities by a microbial cell to exert a significant effect, even when in close contact.

Example 4—Anti-Microbial Effect of Heated and Non-Heated Wood Shavings Derived from Different Tree Species The aim of Example 4 was to determine the antimicrobial effects of heated and non-heated wood shavings derived from a range representative soft and hard wood species.

Methodology

For this experiment, shavings from trunk woods from different soft woods (Pine, Spruce, Cedar) and different hard woods (Beech, Birch, Ash, Sweet chestnut, Red oak), were taken, and the shavings from each were placed in six batches. Three of these batches were heated for 72 h at 140°

C., and the other three were dried at 20° C., giving three replicates for each treatment. Subsequently, 1 g of shavings of each set was placed in a Universal bottle, and each was inoculated with 1 ml of a milky suspension (approx $10^8$ cfu per ml) of *Salmonella enterica*. Inoculated shavings were incubated at 25° C. for 20 h. Subsequently, a 10-fold dilution series (neat—$10^{-8}$) was prepared from the shavings and 0.1 ml of each dilution was plated out onto XLD agar. The numbers of *Salmonella* colonies were counted after 36 hours incubation at 25° C.

Results

The results are shown in Table 5.

TABLE 5

Recovery of *Salmonella enterica* (log cfu $g^{-1}$ wood ± SE) from heated and non-heated wood shavings derived from a selection of soft and hard woods (n = 3). Each replicate was inoculated with approx $10^8$ cfu

| Wood type | Non-Heated | Heated | Significance |
|---|---|---|---|
| Pine (soft) | 6.88 ± 0.11$^c$ | 0 | *** |
| Spruce (soft) | 7.56 ± 0.06$^d$ | 4.50 ± 0.02 | *** |
| Cypress (soft) | 5.24 ± 0.07$^b$ | 0 | *** |
| Ash (hard) | 7.12 ± 0.06$^c$ | 0 | *** |
| Beech (hard) | 6.85 ± 0.19$^c$ | 0 | *** |
| Red Oak (hard) | 7.22 ± 0.13$^c$ | 0 | *** |
| Birch (hard) | 7.32 ± 0.04$^{cd}$ | 0 | *** |
| *Eucalyptus* | 5.93 ± 0.07$^b$ | 5.3 ± 0.06 | *** |
| Sweet chestnut (hard) | 0$^a$ | 0 | NS |
| Significance | *** | *** | |

* Different letters indicate a significant difference between treatments

Conclusions

From the data presented in Table 5, it can be concluded that:
 (i) There were small but significant differences in the antimicrobial properties of non-heated wood shavings. Spruce, Birch and Oak appeared to be the least antimicrobial, since each of these woods allowed the recovery of the greatest number of bacterial colonies. Cyprus and Eucalyptus appeared to be the most antimicrobial when before heat-treatment, since these two woods resulted in fewer bacterial colonies to grow;
 (ii) Heating resulted in a significant increase in the antimicrobial activity of all of the wood species that were tested;
 (iii) Heating resulted in a 3 fold increase in the antimicrobial activity in Eucalyptus, a 1000 fold increase in Spruce, and complete inhibition in each of Pine, Cyprus, Ash, Beach, Oak and Birch; and
 (iv) Besides vanillin, other antimicrobial substances must be present in Pine and Cedar.

Example 5—Toxicity Tests

The aim of this example was to show that the combination dehydro-abietic acid with vanillin (or any other antimicrobial substance derived from wood) is safe for human consumption.

Potential harm caused by a substance is determined by its potential toxicity and its exposure to target cells. Understanding of the potential pathways by which a potentially toxic substance could present itself to a human cell is therefore important for determining potential harm (risk). If it can be shown that the substance (or toxic combination of substances) is unlikely to come into contact with human target cells, then the substance must be regarded as being safe. In the case of dehydro-abietic acid and vanillin (or any other natural anti-microbial agent), there are at least four mechanisms that could prevent exposure of human cells when food coated with the product is ingested, i.e:
 1) Ingestion of the composition will result in a sufficient dilution of the compounds to make them ineffective;
 2) The cells of the digestive system are protected by a layer of mucous that protects the cells of the digestive system against contact with the composition;
 3) One (or both) compounds are inactivated by the digestive system. This could be as a result of enzymatic activity; and
 4) The compounds are not soluble enough in the stomach juices to have any impact on the cells of the digestive system.

Only possibility 4 can be tested without using feeding studies.

Methodology

In this experiment, heated and non-heated pine shavings were used as test materials. Previous research has shown that heated pine shavings become highly antimicrobial. This effect is believed to be at least partly due to the synergistic effects that dehydro-abietic acid has on a number of mildly anti-microbial substances that are formed during mild and prolonged heating (see Examples 1 and 3). If these substances stay associated with the pine shavings and cannot be extracted using water, it can be assumed that they won't solubilise in the digestive system, and will not resulting in any exposure. *Salmonella* was used as the test organism because it has already been demonstrated that *Salmonella* cells are sensitive to the combination of abietic acid and vanillin (see Example 1).

Water Extractions 6 g of material from each set of treated and non-treated pine shavings were soaked in water by adding 5 ml of sterile water to 2 g of shavings (in triplicate) using the following soaking regimes:
 24 hours soaking at room temperature
 24 hours soaking at 90° C. in water bath To assess if the extract was antimicrobial, the following procedure was followed:
 1. Pour 1 ml of extract over 1 g shredded (autoclaved) filter paper (12 samples);
 2. Use, as control, 0.25 strength Ringer's Solution (3 samples);
 3. Dry samples at 50° C. overnight (or till dry);
 4. Prepare a milky suspension of *Salmonella* in 0.25 strength Ringer's Solution and add 1 ml of this to each sample;
 5. Incubate overnight at 30° C.;
 6. Plate out a dilution series ($10^{-1}$-$10^{-6}$) for each (15× 6=90 plates);
 7. Incubate and enumerate countable plates; and
 8. Compare inhibition against control treatment and extracts from non-heated shavings.

To assess the antimicrobial activity of the extracted shavings, the following procedures were followed:
 1. Dry the shavings that were extracted at 50° C. overnight (or till dry);
 2. Use 2 g shredded filter paper as control (3 samples);
 3. Add to each 2 g of shavings and filter paper 2 ml of *Salmonella* suspension;
 4. Incubate at 30° C. for 24 h;
 5. Plate out a dilution series ($10^{-1}$-$10^{-6}$) for each;
 6. Incubate and enumerate countable plates; and 7. Compare inhibition against control (filter paper) and non-heated shavings.

Alcohol Extractions

Take 6 g of material from each treated and non-treated batch and soak by adding 5 ml of methanol to 2 g of shavings (in triplicate) and soak for 24 hours:

To assess if the extract was antimicrobial the following procedure was followed:

1. Pour 1 ml of extract over 1 g of shredded (autoclaved) filter paper (6 samples);
2. Use as control 0.25 strength Ringer's Solution (3 samples);
3. Soak three, 1 g samples with methanol (to ensure that alcohol residues don't inhibit microbial growth);
4. Dry each sample at 50° C. overnight (or till dry);
5. Prepare a milky suspension of Salmonella in 0.25 strength Ringer's Solution and add 1 ml of this to each sample;
6. Incubate overnight at 30° C.;
7. Plate out a dilution series ($10^{-1}$-$10^{-6}$) for each (12×6=72 plates);
8. Incubate and enumerate countable plates; and
9. Compare inhibition against controls and non-heated shavings.

To asses the antimicrobial activity of the extracted shavings, the following procedures were followed:

1. Dry extracted samples at 50° C. overnight (or till dry);
2. Use 2 g shredded filter paper as control (3 samples);
3. Add to each 2 g of shavings and filter paper 2 ml of Salmonella suspension;
4. Incubate at 30° C. for 24 h;
5. Plate out a dilution series ($10^{-1}$-$10^{-6}$) for each (9×6=54 plates);
6. Incubate and enumerate countable plates; and
7. Compare inhibition against control (filter paper) and non-heated shavings.

Results

Tables 6 and 7 show the results.

TABLE 6

Recovery of Salmonella (log cfu $g^{-1}$ ± SE) from inoculated filter paper treated with extracts from heated and non-heated pine shavings. Extracts were obtained by soaking 2 g shavings in cold water (Cold water Extract), water of 90° C. (Hot water Extract) or methanol (Alcohol Extract). Controls were not treated but received the same amount of Salmonella as the treated filter paper (n = 3).

| Treatment | Extracts from Heated shavings | Extracts from Non-heated shavings |
| --- | --- | --- |
| Cold water Extract | 7.54 ± 0.05 a* | 8.14 ± 0.03 ab |
| Hot water Extract | 7.37 ± 0.06 a | 7.94 ± 0.05 bc |
| Alcohol Extract | 4.80 ± 0.11 b | 7.91 ± 0.10 bc |
| Control | 7.63 ± 0.10 a | 7.72 ± 0.09 c |
| Significance | P < 0.001 | P < 0.05 |

*Different letters indicate a significant difference between treatments

TABLE 7

Recovery of Salmonella (log cfu $g^{-1}$ ± SE) from inoculated, heated and non-heated pine shavings that were previously extracted by soaking 2 g shavings in cold water (Cold water Extract), water of 90° C. (Hot water Extract) or methanol (Alcohol Extract). Controls consisted of filter paper that received the same amount of Salmonella as the pine shavings (n = 3)

| Treatment | Extracts from Heated shavings | Extracts from Non-heated shavings |
| --- | --- | --- |
| Cold water Extract | 0.00 ± 0.00 a* | 7.63 ± 0.12 a |
| Hot water Extract | 0.00 ± 0.00 a | 8.02 ± 0.05 a |
| Alcohol Extract | 4.00 ± 0.00 b | 7.06 ± 0.12 b |
| Control | 7.63 ± 0.10 c | 7.72 ± 0.09 a |
| Significance | P < 0.001 | P < 0.001 |

*Different letters indicate a significant difference between treatments

Conclusions

From Tables 6 and 7 it may concluded that:
(i) Both cold and hot water extracts from heated pine shavings were non-toxic to Salmonella;
(ii) Microbial toxicity remained associated with pine shavings after extraction with cold or hot water;
(iii) Alcohol extracts of heated pine shavings are toxic to Salmonella;
(iv) Alcohol extraction removed some of the toxicity associated with heated pine shavings;
(v) Dehydroabietic acid in combination with other antimicrobial substances in heated pine shavings are not soluble enough in water to cause significant toxicity to bacterial cells;
(vi) It is expected that ingestion of food treated with dehydroabietic acid together with a natural anti-microbial agent, such as vanillin, will not lead to significant exposure to human cells.

Example 6—Applications of the Compositions of the Invention

The inventors have applied their surprising observation that the antimicrobial activity of known antimicrobial agents such as vanillin can be dramatically improved upon combination with a terpenoid, to a wide range of applications.

(i) Animal Bedding

They have prepared a liquid formulation of a composition containing both dehydro-abietic acid and vanillin, and then sprayed this formulation on to some existing animal bedding, of the type used in poultry houses. The inventors found that the bedding decreased the levels of infection with Campylobacter and Salmonella, and that chickens raised on the bedding did not show any signs of bacterial infection.

(ii) Mulch

The inventors also produced some mulch which had been immersed in the liquid formulation containing dehydroabietic acid and vanillin and left overnight so that a sufficient amount of the formulation had been absorbed. They then applied the mulch over a patch of soil and carried out tests to confirm that it was able to prevent soil-borne pathogens from infecting plants, fruits or vegetables. They were pleased to see that the treated mulch prevented microbial infection on strawberries that were grown in the mulch when compared to the control when normal mulch was used.

(iii) A Medical Device

The inventors then tested whether it was possible confer antimicrobial activity to the surface of a medical device, and used a wound dressing (i.e. a bandage) as a model. They dipped the bandage in the formulation, and left it over night for it to absorb an active amount. They found to their surprise that the bandage prevented the spread of microorganism infection emanating from a wound underneath the bandage.

(iv) A Textile or Polymer

The formulation was then applied to pieces of cotton and wool, which were then used in the manufacture of articles of clothing. Also, a shoe was produced, and the inventors found that in all cases, microbial infection was prevented. In the case of the footwear, the production of bad odours was also minimised.

(v) A Food Packaging Material

The inventors also sprayed food packaging products, such as cardboard moulds, with the liquid formulation. Perishable foodstuffs such as fruit and vegetables were stored in the packaging material, and the inventors found that the foodstuffs did not rot as quickly as control foodstuffs that had been stored in traditional packaging materials.

Summary

The inventors have demonstrated that molecules with a polar, prolytic group and a rigid hydrophobic moiety can increase the antimicrobial activity of mildly anti-microbial substances that interfere with microbial cell membranes. Terpenoids, such as dehydro-abietic acid, can increase the antimicrobial activity of the antimicrobial agent, vanillin, by 1000-2000 fold. They have also shown that dehydro-abietic acid is poorly-soluble in water and that therefore water extracts from materials that contain both dehydro-abietic acid and vanillin are non-toxic to microbial cells. Instead, the antimicrobial activity remains within the treated material. Accordingly, ingestion of food treated with a terpenoid, such as dehydro-abietic acid, together with a natural antimicrobial agent, such as vanillin, will not lead to significant exposure to human cells.

Example 7—Synergistic Effect of Purified Dehydro-Abietic Acid (DHAA) on Antimicrobial Effect of Commercial Vanillin Against *Salmonella enteritidis* Using a Perlite Bio-Assay As described in the previous examples, significant results were obtained using either dehydro-abietic acid and/or vanillin that had been isolated from heated wood shavings. Experiments that gave up to 2000× greater antimicrobial effects of vanillin (isolated from heated wood) were conducted using a 'perlite-bio-assay' instead of a conventional dilution assay in broth. It could be argued that drying the combination onto perlite and calculating the concentrations based on the weight of the perlite could have biased the results.

This experiment therefore assesses if the perlite bio-assay biases the results using pure DHAA that had been isolated from disproportionated rosin, and pure vanillin purchased from Sigma-Aldrich.

Preparation of Stock solutions: A 20 mM stock solution of vanillin was made in acetone and diluted further by two-fold dilution to make a concentration range between 20 to 0.078 mM. Also, one 20 mM stock solution of DHAA was made in acetone.

Bioassay test: The test was carried out using 1.5 ml Eppendorf tubes containing 10 mg of fine perlite. Ten µl of each concentration of vanillin was dispensed into four Eppendorf tubes to obtain four replicates of each concentration. Two of these received 10 µl of DHAA. The tubes were left in laminar flow chamber for 3 h to allow evaporation of the acetone. Subsequently, each tube received 1 µl of an overnight culture of *Salmonella enteritidis*. To keep the perlite moist during incubation, 10 µl of sterile R.O water was dispensed into each tube. As controls, two tubes received DHAA only and two tubes received R.O water only.

The tubes were incubated overnight, and bacterial survival was quantified by plating the content of each tube onto nutrient agar for the bacterial count.

Results

TABLE 8

Effect of DHAA on vanillin antimicrobial activity against *Salmonella enteritidis* (CFU/tube)

| | 10 mM | 5 mM | 2.5 mM | 1.25 mM | 0.625 mM | 0.313 mM |
|---|---|---|---|---|---|---|
| Rep1(+DA) | — | — | 305 | 480 | TMTC | TMTC |
| Rep2(+DA | — | — | 341 | 500 | TMTC | TMTC |
| Rep 1 | 500 | TMTC | TMTC | TMTC | TMTC | TMTC |
| Rep 2 | 394 | TMTC | TMTC | TMTC | TMTC | TMTC |

DHAA: TMTC
R.O controls: TMTC

Conclusions

In this experiment DHAA made vanillin approximately eight times more effective. The perlite bio-assay therefore clearly provides valid results on the activity of anti-microbial agents, and demonstrates synergism between the two pure compounds tested. Also, the inventors believe that there may be certain unknown factors that can further contribute to the synergistic activity of DHAA and vanillin when these compounds are isolated from heated wood shavings.

Example 8—Determination of Minimum Inhibitory Concentrations (MICs) of Dehydrozingeron and Coniferaldehyde in Combination with Vanillin and DHAA Mixtures Against *Salmonella enteritidis*

It was noted that combining pure dehydroabietic acid (DHAA) and pure vanillin resulted in anti-microbial synergism between the two compounds (i.e. 8×), though not to such an extent as that observed when combining vanillin and DHAA isolated from heated pine wood (i.e. 2000×). Similar strong anti-microbial effects were obtained if only one of the components came from heated pine wood and the other was obtained from a commercial source in a pure form. Interestingly, anti-microbial effects obtained in this way resulted in an orange colour of the mix, suggesting that an unknown contaminant with a orange yellow colour could have been involved in augmenting the synergistic effects between vanillin and DHAA. A potential candidate molecule was thought to be coniferaldehyde which had previously been isolated from heated pine shavings.

Similarly, if vanililin was not used immediately but was stored in acetone, the antimicrobial effects of combining DHAA with vanillin was largely restored. It is known that vanillin reacts with acetone to form a ketone, i.e. dehydrozingerone. It was therefore hypothesised that dehydrozingerone could also play a role in the antimicrobial effect obtained between DHAA and vanillin.

Materials & Methods:

Pure vanillin was obtained from Sigma-Aldrich. Dehydrozingerone was made by condensing vanillin with acetone. Pure dehydroabietic acid was isolated from disproportionated rosin.

A 20 mM stock solution of vanillin was made to make the final concentrations. Also 0.1, 1, 5 and 10 mM stock solutions of dehydrozingerone and 20 mM stock solution of DHAA were made by dissolving the compounds in acetone. Stock solutions were stored at 5° C. in a fridge.

In vitro bioassay: The minimum inhibiting concentration (MIC) of vanillin in combination with potential synergistic molecules was determined using a micro-broth dilution method. Six two fold dilution series of vanillin were prepared by diluting with sterile nutrient broth, using 96-well micro-titre plates in order to obtain a 2 fold dilution series of 20 mM to 0.078 mM vanillin. Four different concentrations (10 mM, 5 mM, 1 mM and 0.1 mM) of dehydrozingerone (DHZ) were made and combined with the different concentrations of vanillin by adding 100 µl of each stock solution to each well. In a separate experiment, DHZ was replaced by coniferaldehyde. Control wells were prepared by adding 100 µl acetone. Each treatment was replicated four times. The plates were kept in a laminar flow chamber for 8 hours to allow evaporation of the acetone. To determine anti-microbial activity in each well, plates were inoculated with 5 µl of a bacterial cell culture containing $10^8$ cfu/ml *Salmonella enteritidis* that had grown overnight at 25° C. After inoculation, the plates were incubated at 25° C. for 24 hours. To determine if treatments were bacteriocidal, 0.01 ml from each well was spotted onto nutrient agar. Thus, inoculated nutrient agar plates were incubated for 24-48 h and spots with no bacterial growth or just a few colonies were marked as 'bacteriocidal'. To determine a bacteriostatic effect, a tetrazolium salt solution was added to each well to determine metabolic activity. After overnight incubation at 25° C. no change in colour was defined as a bacteriostatic effect while metabolism (no effect) was indicated as a red to purple colour.

Results

TABLE 9

Effect of combining different concentrations of coniferaldehyde and Vanillin on growth of *Salmonella enteritidis*. All treatments contained 20 mM dehydroabietic acid, except the control (−DHAA). (n = 4)

| Coniferyl aldehyde Concentration | Vanillin Concentration (mM) | | | | | | | | |
|---|---|---|---|---|---|---|---|---|---|
| (mM) | 20 | 10 | 5 | 2.5 | 1.25 | 0.625 | 0.312 | 0.156 | 0.078 |
| 10 | BC | BC | BC | BC | BC | BC | BC | BC | BC |
| 5 | BC | BC | BC | BC | BC | BC | BS | BS | BS |
| 1 | BS | BS | BS | BS | BS | BS | G | G | G |
| 0.1 | BS | BS | BS | G | G | G | G | G | G |
| 0.0 | BS | BS | BS | G | G | G | G | G | G |
| 0.0-DHAA | BS | BS | G | G | G | G | G | G | G |

BS: Bacteriostatic
BC: Bactericidal
G: Growth

TABLE 10

Effect of combining different concentrations of Dehydrozingeron and Vanillin on growth of *Salmonella enteritidis*. All treatments contained 20 mM dehydroabietic acid, except the control (−DHAA). (n = 4)

| Dehydrozingeron Concentration | Vanillin Concentration (mM) | | | | | | | | |
|---|---|---|---|---|---|---|---|---|---|
| (mM) | 20 | 10 | 5 | 2.5 | 1.25 | 0.625 | 0.312 | 0.156 | 0.078 |
| 10 | BC | BC | BS | BS | BS | BS | BS | BS | BS |
| 5 | BS | BS | BS | BS | BS | BS | BS | BS | BS |
| 1 | BS | BS | BS | G | G | G | G | G | G |
| 0.1 | BS | BS | BS | G | G | G | G | G | G |
| 0.0 | BS | BS | BS | G | G | G | G | G | G |
| 0.0-DHAA | BS | BS | G | G | G | G | G | G | G |

BS: Bacteriostatic;
BC: Bactericidal;
G: Growth

Conclusions

Coniferaldehyde is an effective anti-microbial agent that in combination with vanillin and DHAA confers strong anti-microbial effects against *Salmonella enteritidis*. Dehydrozingerone is a mild anti-microbial agent that in combination with vanillin and DHAA confers strong anti-microbial effects against *Salmonella enteritidis*. The results suggest that a combined concentration of >5 mM of vanillin and dehydrozingerone is required (in combination with DHAA) to be bacteriostatic.

Example 9—Role of Dehydroabietic Acid in Anti-Microbial Activity Between Coniferaldehyde and Vanillin In the previous experiments DHAA was added to combinations of vanillin and coniferaldehyde. To determine if DHAA is essential, a separate experiment was set up to quantify its role in the anti-microbial effect of the three substances.

Materials & Methods

Vanillin and coniferaldehyde were obtained from Sigma-Aldrich. Dehydroabietic acid was isolated from disproportionated rosin using column chromatography.

A 20 mM stock solution of vanillin in deionised water was prepared. Stock solutions of 5 and 10 mM coniferaldehyde and 20 mM dehydroabietic acid (DHAA) were prepared in acetone. All stock solutions were stored at 5° C.

In vitro bioassay: The MIC of the different treatments was determined using a micro broth dilution method. A 4 fold dilution series of vanillin was prepared by diluting the 20 mM stock solution with sterile water to obtain concentrations between 20 mM to 0.0002 mM vanillin using a 96-well micro-titre plate. Two concentrations of 5 and 10 mM coniferaldehyde were prepared and combined with the different concentrations of vanillin by adding 100 µL of each stock solution to each well. Control wells were prepared by adding 100 µL acetone. Half the wells received DHAA to a final concentration of 20 mM while the other half did not. Each treatment was replicated four times. The plates were placed in a laminar flow chamber for 8 hours to evaporate the solvent. Subsequently, each well was inoculated with 5 µl of a *Salmonella enteritidis* suspension containing $10^8$ cfu/ml that had grown overnight at 25° C. After inoculation, the plates were incubated at 25° C. for 24 hours. To determine if treatments were bacteriocidal, 0.01 ml from each well was spotted onto nutrient agar. Plates were incubated for 24-48 h and spots with no bacterial growth or just a few colonies were marked as 'bacteriocidal'. Where possible, colonies were counted to obtain more precise quantitative data. To determine a bacteriostatic effect 50 µl tetrazolium salt solution was added to each well to determine metabolic activity. After overnight incubation at 25° C., no change in colour was defined as a bacteriostatic effect while metabolism (no effect) was indicated by a red to purple colour.

Results

TABLE 11

Anti-microbial effect of vanillin in combination with Coniferyl aldehyde (CFA) with and without 20 mM Dehydroabietic Acid (DHAA). Treatments were tested against *Salmonella enteritidis*. (n = 4)

| Coniferyl aldehyde (CFA) | Vanillin concentration (mM) | | | | | | | | Dehydroabietic acid (DHAA) |
|---|---|---|---|---|---|---|---|---|---|
| | 20 | 5 | 1.25 | 0.312 | 0.078 | 0.019 | 0.001 | 0.0002 | |
| 10 mM CFA | BC | BC | BC | BC | BC | BC | BC | BC | |
| 10 mM CFA + 20 mM DHAA | BC | BC | BC | BC | BC | BC | BC | BC | |
| 5 mM CFA | BS | BS | BS | BS | BS | BS | BS | BS | |
| 5 mM CFA + 20 mM DHAA | BC | BC | BC | BC | BC | BS | BS | BS | |
| 20 mM DHAA | BS | G | G | G | G | G | G | G | |

BS: bacteriostatic;
BC: bactericidal;
G: growth

TABLE 12

Colony counts obtained 96 well results plate map for 5 mM coniferaldehyde in combination with vanillin at concentration range between 20-0.00029 mM (4 down cells) and Vanillin/DHAA(4 top cells)

| Concentration (mM) Vanilin/Coniferylaldehyde | | | | | | | | | | |
|---|---|---|---|---|---|---|---|---|---|---|
| 20/5 | 5/5 | 1.25/5 | 0.31/5 | 0.078/5 | 0.019/5 | 0.004/5 | 0.001/5 | 0.00029/5 | 0/5 | 0/0 |
| +DHAA 20 mM | | | | | | | | | | |
| 0 | 0 | 0 | 0 | 2 | 6 | 11 | 36 | 34 | TMTC | TMTC |
| 0 | 0 | 0 | 0 | 1 | 8 | 18 | 30 | 30 | TMTC | TMTC |
| 0 | 0 | 0 | 0 | 1 | 8 | 21 | 41 | 25 | TMTC | TMTC |
| 0 | 0 | 0 | 0 | 2 | 8 | 20 | 35 | 38 | TMTC | TMTC |
| 6 | 11 | 21 | 34 | 50 | TMTC | TMTC | TMTC | TMTC | TMTC | TMTC |
| 8 | 0 | 25 | 34 | 52 | TMTC | TMTC | TMTC | TMTC | TMTC | TMTC |
| 6 | 8 | 19 | 29 | 56 | TMTC | TMTC | TMTC | TMTC | TMTC | TMTC |
| 5 | 19 | 20 | 30 | 48 | TMTC | TMTC | TMTC | TMTC | TMTC | TMTC |

Conclusions

Dehydro-abietic acid confers a synergistic effect on the activity of combinations of coniferaldehyde and vanillin. The presence of small concentrations of vanillin (at least 0.0003 mM) is required to make 5 mM coniferaldehyde bacteriocidal (if DHAA is present at 20 mM).

Example 10—Effect of Dehydrozingerone on Mixtures of Vanillin and Dehydro-Abietic Acid (DHAA) Against *Salmonella enteritidis*

Previously, it was suggested that dehydrozingerone (formed from vanillin) could be a contributing factor explaining antimicrobial activity of heated wood shavings. In experiments where both vanillin and dehydrozingerone were used in combination with dehydro-abietic acid it was suggested that the anti-microbial activity of the two molecules was additive. Here, the inventors investigated if this was the case or if there were synergistic effects depending on the ratio of the two.

Materials & Methods

Vanillin was obtained from Sigma-Aldrich. Dehydrozingerone was made by condensing vanillin with acetone as follows: 0.5 g of vanillin was added to 2 ml acetone and shaken in a screw-top vial to dissolve the vanillin. After the vanillin had dissolved, 1 ml 10% (w/v) aqueous NaOH was added. The mixture was then stored at room temperature for 24 hours. Subsequently, 10 ml, 3 M aqueous HCL was added and the mixture was shaken vigorously to allow the formation of yellow crystals of dehydrozingerone. Purified dehydrozingerone was isolated by filtering the thus obtained suspension of dehydrozingerone using a Buchner funnel followed by rinsing the crystals with water. After air-drying the material, the structure of the isolated dehydrozingerone was confirmed using NMR.

Preparation of Vanillin-Dehydrozingerone Solutions

Solutions containing vanillin and Dehydrozingerone with the ratios (w/w), 100:0, 75:25, 50:50, 25:75, 0:100, were prepared in 5 ml of Acetone. Undiluted the combined concentration of dehydrozingerone and vanillin was 10 mM. 20 mM dehydroabietic acid was added to each treatment by adding 30.4 mg of to each ratio prior to antimicrobial testing. Control treatments consisted of DHAA alone and solvent only. The stock solutions were stored in the fridge at 5° C. for 48 hours.

Assay Method

The inhibitory activities of combined vanillin and dehydrozingerone solutions were determined by micro dilution broth method. 96 well plates were filled with 9.6 mL nutrition broth. In order to determine the MIC (minimum inhibitory concentration) of the samples, several dilutions of the samples were made (0, 1:2, 1:4, 1:8, 1:16, 1:32, 1:64, 1:128) into the broth. After making the dilution series, plates were left in a laminar flow cabinet for 5 hours to allow the solvent to evaporate.

Subsequently, each well was inoculated with 5 µl of a *Salmonella enteritidis* suspension containing $10^8$ cfu/ml that had grown overnight at 25° C. After inoculation, the plates were incubated at 25° C. for 24 hours. To determine if treatments were bacteriocidal, 0.01 ml from each well was spotted onto nutrient agar. Plates were incubated for 24-48 h and spots with no bacterial growth or just a few colonies were marked as 'bacteriocidal'. Where possible, colonies were counted to obtain more precise quantitative data. To determine a bacteriostatic effect, 50 µl tetrazolium salt solution was added to each well to determine metabolic activity. After overnight incubation at 25° C. no change in colour was defined as a bacteriostatic effect while metabolism (no effect) was indicated by a red to purple colour.

TABLE 13

Anti-microbial effect of vanillin in combination with hydrozingerone in the presence of 20 mM Dehydro-abietic Acid (DHAA). Treatments were tested against *Salmonella enteritidis*. (n = 4)

| Ratios Vanillin:Dehydrozingeron | Serial dilutions | | | | | | | |
|---|---|---|---|---|---|---|---|---|
| (mM) | 1 | 1:2 | 1:4 | 1:8 | 1:16 | 1:32 | 1:64 | 1:128 |
| 100:00 | BS | BS | G | G | G | G | G | G |
| 75:25 | BC | BS | BS | BS | BS | G | G | G |
| 50:50 | BS | BS | G | G | G | G | G | G |
| 25:75 | BS | BS | BS | BS | G | G | G | G |
| 00:100 | BS | BS | G | G | G | G | G | G |

BS: Bacteriostatic;
BC: Bactericidal;
G: Growth

Conclusions

The combined effect of hydrozingerone and vanillin was not additive, but depended on the ratio between the two molecules. Best results were obtained when at a ratio of 1:3 of either molecule was used. On their own, hydrozingerone and vanillin had a similar anti-microbial activity, but combined at a ratio of 1 in 3, the surprising effect was 4 to 8 times greater than when used alone or at a 50:50 ratio.

Example 11—Effect of pH on the Solubility of Dehydro-Abietic Acid and Effect of Storage Condition of Stock Solution on Anti-Microbial Activity of Combinations of Vanillin and Dehydro-Abietic Acid Against *Salmonella enteritidis*

It was noted that combining dehydroabietic acid and vanillin at high pH (>9) caused the combination to become less effective. It was hypothesised that this could be due to the low solubility of dehydro-abietic acid under alkaline conditions (resulting in dehydro-abietic acid falling out of solution). Most experiments described so far were conducted at pH 7 which gave good activity, but not as good as the extracts taken directly from heated wood shavings. Heated shavings have a pH of around 4. However, such a low pH could affect bacterial growth which is normally more favourable at neutral pH. To test the effect of pH while ensuring that DHAA was dissolved, two methods of dissolving the compound were used. In one, the compound was dissolved in a phosphate buffer with a pH of 4, and in the other treatment, DMSO was used with a pH of 7.

The following treatments were tested:

Vanillin stock solution, made 48 hours before the start of the experiment; solution kept in fridge at 5° C.;

Dehydroabietic acid (DHAA) stock solution, made 48 hours before the start of the experiment; solution kept in fridge at 5° C.;

Combination of Vanillin/DHAA stock solutions, made 48 hours before the start of the experiment; solution kept in fridge at 5° C.;

Vanillin stock solution, made 48 hours before the start of the experiment and kept at room temperature (20° C.);

DHAA stock solution, made 48 hours before the start of the experiment and kept at room temperature (20° C.); and Combination of vanillin/DHAA stock solutions, made 48 hours before the start of the experiment and kept at room temperature (20° C.).

Materials & Methods

Vanillin was obtained from Sigma-Aldrich and DHAA was isolated from disproportionated rosin.

Stock solution in buffer based broth at PH 4: Two batches of a 20 mM stock solution of vanillin and two batches of vanillin/DHAA (10 mM/20 mM) were made in acetone. One of each batch was kept in fridge and the other was kept at room temperature.

Stock solution testing in buffer based broth at pH 7: Two batches of a 20 mM stock solution of vanillin and two batches of vanillin/DHAA (10 mM/20 mM) were made in DMSO. One of each batch was kept in fridge and the other was kept at room temperature.

Bioassay test: The test was carried out using a micro-broth dilution technique. Vanillin and vanillin/DHAA stock solutions were diluted further down in a two fold dilution series to make a concentration range between 10 mM-0.625 mM. 100 μL of each concentration was added to 100 μL of nutrient broth in each well of a 96 well plate. Three replicates were made for each concentration. Plates were kept in a laminar chamber to allow evaporation of the solvent.

Subsequently, each well was inoculated with 5 μl of a *Salmonella enteritidis* suspension containing $10^8$ cfu/ml that had grown overnight at 25° C. After inoculation, the plates were incubated at 25° C. for 24 hours. To determine if treatments were bacteriocidal, 0.01 ml from each well was spotted onto nutrient agar. Plates were incubated for 24-48 h and spots with no bacterial growth or just a few colonies were marked as 'bacteriocidal'. Where possible, colonies were counted to obtain more precise quantitative data. To determine a bacteriostatic effect 50 μl tetrazolium salt solution was added to each well to determine metabolic activity. After overnight incubation at 25° C. no change in colour was defined as a bacteriostatic effect while metabolism (no effect) was indicated by a red to purple colour.

TABLE 14

Effect of pH, and potential interaction of vanillin and dehydroabietic acid (DHAA) on the growth of *Salmonella enteritidis*. DHAA was either added at the beginning of the experiment (alone) or allowed to interact with vanillin for 48 h (combination) prior to the start of the experiment (n = 3)

| | | | Treatment | Vanillin [Mm] | | | | |
|---|---|---|---|---|---|---|---|---|
| pH | Temp [° C.] | DHAA [Mm] | | 10 | 5 | 2.5 | 1.25 | 0.625 |
| 4 | 4 | 20 | Alone | BS | BS | BS | G | G |
| | | 20 | Combination | BC | BS | BS | BS | G |
| | | 0 | | BS | G | G | G | G |
| 4 | 20 | 20 | Alone | BS | BS | BS | BS | G |
| | | 20 | Combination | BC | BS | BS | BS | G |
| | | 0 | | BS | G | G | G | G |
| 7 | 4 | 20 | Alone | BS | BS | BS | G | G |
| | | 20 | Combination | BC | BS | BS | BS | G |
| | | 0 | | BS | G | G | G | G |
| 7 | 20 | 20 | Alone | BS | BS | BS | BS | G |
| | | 20 | Combination | BC | BS | BS | BS | G |
| | | 0 | | BS | G | G | G | G |

BC: Bactericidal;
BS: Bacteriostatic;
G: Growth

Conclusions

Dehydro-abietic acid increases the anti-microbial activity of vanillin at both pH 4 and pH 7 (pH itself had little effect on the survival of *Salmonella*). Allowing dehydro-abietic acid to interact with vanillin for 48 hours increases the anti-microbial activity of the two molecules.

Example 12—Synergistic Effect of DHAA on Coniferaldehyde, Thymol and Stilbene In the previous experiments, anti-microbial compounds were tested in conjunction with vanillin making it difficult to determine if DHAA increased the activity of just vanillin or also that of other natural antimicrobial molecules such as thymol, coniferaldehyde and stilbene. In the first test, these compounds were tested against the Gram-negative bacterium *Salmonella enteritidis*, and in a second test the same compounds were tested against the Gram-positive bacterium *Staphylococcus aureus*.

Materials & Methods

Thymol, Trans-stilbene and Coniferaldehyde were obtained from Sigma-Aldrich. Dehydroabietic acid was isolated from disproportionated rosin.

Bioassay test: The test was carried out using a micro-broth dilution technique. DHAA (20 mM) was combined with either coniferaldehyde, thymol or (trans) stilbene and incubated for 48 h at 25° C. Control solutions were made up of coniferaldehyde, thymol and stilbene without dehydro-abietic acid. A solvent control with just acetone was also prepared. For the test, solutions were diluted in a two fold dilution series to make a concentration range between 10-0.156 mM active ingredient. Each concentration was then amended with dehydro-abietic acid to give a final concentration of 20 mM dehydro-abietic acid. 100 µL of each concentration was added to 100 µL of nutrient broth in each well of a 96 well plate. Three replicates were made for each concentration. Plates were kept in laminar chamber to allow evaporation of the solvent.

Subsequently, each well was inoculated with 5 µl of a *Salmonella enteritidis* suspension containing $10^8$ cfu/ml that had grown overnight at 25° C. In the second test *Staphylococcus aureus* was used. After inoculation, the plates were incubated at 25° C. for 24 hours. To determine if treatments were bacteriocidal, 0.01 ml from each well was spotted onto nutrient agar. Plates were incubated for 24 h and spots with no bacterial growth or just a few colonies were marked as 'bacteriocidal'. To determine a bacteriostatic effect 50 µl tetrazolium salt solution was added to each well to determine metabolic activity. After overnight incubation at 25° C. no change in colour was defined as a bacteriostatic effect while metabolism (no effect) was indicated by a red to purple colour.

Results

TABLE 15

Synergistic effect of DHAA on coniferaldehyde, thymol or stilbene against *Salmonella enteritidis*. Treatments with DHAA contained 20 mM DHAA. (n = 3)

| Treatments | Serial dilutions (20 mM-0.156 mM) | | | | | | |
|---|---|---|---|---|---|---|---|
| | 10 | 5 | 2.5 | 1.25 | 0.625 | 0.313 | 0.156 |
| Coniferyl aldehyde + DHAA | BC | BC | BS | BS | BS | BS | G |
| Coniferyl aldehyde | BC | BS | G | G | G | G | G |
| Thymol + DHAA | BC | BC | BC | BC | BC | G | G |
| Thymol | BC | BC | BC | BC | G | G | G |
| Stilbene + DHAA | BC | G | G | G | G | G | G |
| Stilbene | G | G | G | G | G | G | G |

BC: Bactericidal,
BS: Bacteriostatic,
G: Growth

Results

DHAA acid had a strong synergistic activity on coniferaldehyde, making the compound around 16 times more effective against *Salmonella enteritidis*. DHAA made thymol around twice as effective against *Salmonella enteritidis*.

Example 13—Antimicrobial Activity of Combinations of Dehydro-Abietic Acid and Vanillin Against a Variety of Micro-Organisms The inventors tested the antimicrobial activity of a number of different compounds on micro-organisms (Gram-positive and Gram-negative bacteria, filamentous fungi and yeast) using inhibition zone experiments on thin layer chromatography (TLC) paper.

Materials and Methods

Two test solutions were prepared, i.e.: (i) vanillin in combination with DHAA, and (ii) stilbene in combination with dehydro-abietic acid (DHAA). The activity of the solutions were then tested on several different micro-organisms, as follows.

A droplet of a test solution was placed on a TLC plate. The solvent was allowed to evaporate and a suspension of test micro-organisms (Gram-positive and Gram-negative bacteria) in broth was applied evenly onto the TLC plate. The plate was incubated overnight. To visualise microbial activity, the TLC plate was sprayed with tetrazolium salt solution. Microbial activity was indicated by a red-pink colour.

To show the efficacy of the solutions against filamentous fungi, the inoculated TLC plates were incubated until the fungus started to sporulate. To show efficacy against yeast, after incubation, the TLC plates were pressed against a nutrient agar plate. The plate was incubated until yeast colonies were clearly visible.

Results

FIGS. 1-8 show the effects of the test solutions on the growth of the organisms that were tested.

Referring to FIG. 1, there is shown the activity of a combination of vanillin and DHAA on *S. aureus*. A clear zone of inhibition is shown in the test compared to the control whether bacterial growth is prevalent. FIG. 2 shows that a combination of stilbene and DHAA is significantly more antimicrobial against *S. aureus* than stilbene on its own, and the control. FIG. 3 shows that a combination of vanillin and DHAA is antimicrobial against *S. enteritidis*, and that these two compounds on their own are ineffective. FIG. 4 shows that a combination of vanillin and DHAA is antimicrobial against *S. typhimurium*.

FIG. 5 shows that a combination of vanillin and DHAA is antimicrobial against *E. coli*. FIG. 6 shows that a combination of vanillin and DHAA is antimicrobial against the filamentous fungus, *Penicillium* spp. FIG. 7 shows that a combination of vanillin and DHAA is antimicrobial against *Aspergillus* spp. Finally, FIG. 8 shows that a combination of vanillin and DHAA is antimicrobial against the yeast, *S. cerevisiae*. Vanillin on its own is effective at 5 mM, but in combination with DHAA, it is effective at only 0.078 mM.

What is claimed is:

1. An antimicrobial composition comprising dehydroabietic acid (DHAA) and an antimicrobial agent selected from the group consisting of vanillin, coniferaldehyde, thymol and stilbene; wherein
   when the antimicrobial agent is vanillin, the ratio of vanillin to DHAA is from 1:1 to 1:1024;
   when the antimicrobial agent is coniferaldehyde, the ratio of coniferaldehyde to DHAA is from 1:4 to 1:64;

when the antimicrobial agent is thymol, the ratio of thymol to DHAA is from 1:32; and when the antimicrobial agent is stilbene, the ratio of stilbene to DHAA is 1:2.

2. A liquid formulation comprising the antimicrobial composition according to claim 1.

3. A method of preventing or inhibiting microbial colonization of an object, which method comprises contacting or coating a surface of the object with the antimicrobial composition according to claim 1.

4. An object comprising the antimicrobial composition according to claim 1.

5. The object according to claim 4, wherein the object is a medical device.

6. The object according to claim 4, wherein the medical device is selected from the group consisting of a catheter, a stent, a wound dressing, a bandage, a contraceptive device, a surgical implant, a replacement joint, contact lens, a bandage, a wound dressing, and a plaster.

7. A method for preventing or inhibiting microbial infection of a food product comprising:

contacting or coating a surface of a food product with the antimicrobial composition according to claim 1.

* * * * *